US012678489B2

(12) United States Patent
Wu et al.

(10) Patent No.: US 12,678,489 B2
(45) Date of Patent: Jul. 14, 2026

(54) MULTI-RECEPTOR AGONIST AND MEDICAL USE THEREOF

(71) Applicants: JIANGSU HANSOH PHARMACEUTICAL GROUP CO., LTD., Jiangsu (CN); SHANGHAI HANSOH BIOMEDICAL CO., LTD., Shanghai (CN)

(72) Inventors: Fangzhou Wu, Jiangsu (CN); Lei Wang, Jiangsu (CN); Xiao Liu, Jiangsu (CN); Ran Wu, Jiangsu (CN); Haiqing Hua, Jiangsu (CN); Rudi Bao, Jiangsu (CN); Xiaolei Wang, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

( * ) Notice: Subject to any disclaimer, the term of this patent is extended or adjusted under 35 U.S.C. 154(b) by 1012 days.

(21) Appl. No.: 17/594,259

(22) PCT Filed: Apr. 10, 2020

(86) PCT No.: PCT/CN2020/084247
§ 371 (c)(1),
(2) Date: Oct. 8, 2021

(87) PCT Pub. No.: WO2020/207477
PCT Pub. Date: Oct. 15, 2020

(65) Prior Publication Data
US 2022/0168396 A1 Jun. 2, 2022

(30) Foreign Application Priority Data

Apr. 11, 2019 (CN) .......................... 201910290162.6
Nov. 15, 2019 (CN) .......................... 201911120906.6

(51) Int. Cl.
| | |
|---|---|
| A61K 38/26 | (2006.01) |
| A61K 31/155 | (2006.01) |
| A61K 31/64 | (2006.01) |
| A61K 45/06 | (2006.01) |
| A61P 3/10 | (2006.01) |
| C07K 14/605 | (2006.01) |

(52) U.S. Cl.
CPC ............ *A61K 38/26* (2013.01); *A61K 31/155* (2013.01); *A61K 31/64* (2013.01); *A61K 45/06* (2013.01); *A61P 3/10* (2018.01); *C07K 14/605* (2013.01)

(58) Field of Classification Search
CPC ...... A61K 38/26; A61K 31/155; A61K 31/64; A61K 45/06; A61P 3/10; C07K 14/605
See application file for complete search history.

(56) References Cited

U.S. PATENT DOCUMENTS

| | | | |
|---|---|---|---|
| 2015/0051141 A9 | 2/2015 | Shandler et al. | |
| 2016/0015788 A1 | 1/2016 | Holscher | |

FOREIGN PATENT DOCUMENTS

| | | |
|---|---|---|
| CN | 101987868 A | 3/2011 |
| CN | 102802657 A | 11/2012 |
| CN | 103861089 A | 6/2014 |
| CN | 104470948 A | 3/2015 |
| CN | 104902920 A | 9/2015 |
| CN | 107001439 A | 8/2017 |
| EP | 2460825 A1 | 6/2012 |
| JP | 2008-533105 A | 8/2008 |
| JP | 2011-524419 A | 9/2011 |
| JP | 2012-530145 A | 11/2012 |
| JP | 2014-507402 A | 3/2014 |
| JP | 2017-534676 A | 11/2017 |
| WO | 2006097537 A2 | 9/2006 |
| WO | 2009155258 A2 | 2/2010 |
| WO | 2010142665 A1 | 12/2010 |
| WO | 2010148089 A1 | 12/2010 |
| WO | 2011012080 A1 | 2/2011 |
| WO | 2012088116 A2 | 11/2012 |
| WO | 2012167744 A1 | 12/2012 |
| WO | 2013164483 A1 | 11/2013 |
| WO | 2014096150 A1 | 6/2014 |
| WO | 2015095684 A1 | 6/2015 |
| WO | 201649190 A1 | 3/2016 |
| WO | 2016066744 A2 | 5/2016 |
| WO | 2018109162 A1 | 6/2018 |

OTHER PUBLICATIONS

International Search Report issued Jul. 9, 2020 in corresponding PCT/CN2020/084247.
Lau, J., et al., "Discovery of the Once-Weekly Glucagon-Like Peptide-1 (GLP-1) Analogue Semaglutide," J. Med. Chem., vol. 58, pp. 7370-7380, Aug. 26, 2015.
Tschop, M.H., et al., "Unimolecular Polypharmacy for Treatment of Diabetes and Obesity," Cell Metabolism, vol. 24, pp. 51-62, Jul. 12, 2016.
Written Opinion issued Jul. 6, 2020 in corresponding PCT/CN2020/084247.

*Primary Examiner* — Julie Ha
*Assistant Examiner* — Erinne R Dabkowski
(74) *Attorney, Agent, or Firm* — Fox Rothschild LLP; Liang Zeng Yan

(57) ABSTRACT

A series of pharmaceutical compositions containing polypeptide dual agonist compounds and pharmaceutically acceptable salts thereof, wherein same have dual agonist effects on a human glucagon-like peptide-1 (GLP-1) receptor and a human blood glucose-dependent insulinotropic polypeptide (GIP) receptor, and can be used for treating non-insulin-dependent diabetes, insulin-dependent diabetes, obesity and other related diseases.

19 Claims, No Drawings
Specification includes a Sequence Listing.

```
                    SEQUENCE LISTING

<160> NUMBER OF SEQ ID NOS: 84

<210> SEQ ID NO 1
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 1

His Xaa Glu Gly Thr Phe Thr Ser Asp Val Ser Ser Tyr Leu Glu Glu
1               5                   10                  15

Glu Ala Ala Lys Glu Phe Ile Ala Trp Leu Val Arg Gly Gly Pro Ser
            20                  25                  30

Ser Gly Ala Pro Pro Pro Ser Lys
        35                  40

<210> SEQ ID NO 2
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 2

Tyr Xaa Glu Gly Thr Phe Thr Ser Asp Val Ser Ser Tyr Leu Glu Glu
1               5                   10                  15

Glu Ala Ala Lys Glu Phe Ile Ala Trp Leu Val Arg Gly Gly Pro Ser
            20                  25                  30

Ser Gly Ala Pro Pro Pro Ser Lys
        35                  40

<210> SEQ ID NO 3
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 3

Tyr Xaa Glu Gly Thr Phe Thr Ser Asp Val Ser Ser Tyr Leu Glu Glu
1               5                   10                  15

Glu His Gln Lys Glu Phe Ile Ala Trp Leu Val Arg Gly Gly Pro Ser
```

-continued

```
            20                25                30

Ser Gly Ala Pro Pro Pro Ser Lys
        35                40

<210> SEQ ID NO 4
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 4

Tyr Xaa Glu Gly Thr Phe Thr Ser Asp Val Ser Ser Tyr Leu Glu Glu
1               5                   10                  15

Ile His Gln Lys Glu Phe Ile Ala Trp Leu Val Arg Gly Gly Pro Ser
            20                  25                  30

Ser Gly Ala Pro Pro Pro Ser Lys
        35                40

<210> SEQ ID NO 5
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 5

His Xaa Glu Gly Thr Phe Thr Ser Asp Val Ser Ser Tyr Leu Glu Glu
1               5                   10                  15

Glu Ala Ala Lys Glu Phe Val Asn Trp Leu Leu Ala Gly Gly Pro Ser
            20                  25                  30

Ser Gly Ala Pro Pro Pro Ser Lys
        35                40

<210> SEQ ID NO 6
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 6

Tyr Xaa Glu Gly Thr Phe Thr Ser Asp Val Ser Ser Tyr Leu Glu Glu
1               5                   10                  15

Glu Ala Ala Lys Glu Phe Val Asn Trp Leu Leu Ala Gly Gly Pro Ser
            20                  25                  30

Ser Gly Ala Pro Pro Pro Ser Lys
        35                40
```

```
<210> SEQ ID NO 7
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 7

Tyr Xaa Glu Gly Thr Phe Thr Ser Asp Val Ser Ile Tyr Leu Glu Lys
1               5                   10                  15

Glu Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 8
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 8

Tyr Xaa Glu Gly Thr Phe Thr Ser Asp Val Ser Ile Tyr Leu Glu Lys
1               5                   10                  15

Glu Ala Ala Glu Glu Phe Val Asn Trp Leu Leu Ala Gly Gly Pro Ser
            20                  25                  30

Ser Gly Ala Pro Pro Pro Ser Lys
        35                  40

<210> SEQ ID NO 9
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 9

Tyr Xaa Glu Gly Thr Phe Thr Ser Asp Tyr Ser Ile Tyr Leu Glu Lys
1               5                   10                  15

Glu Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 10
<211> LENGTH: 40
```

-continued

```
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 10

Tyr Xaa Glu Gly Thr Phe Thr Ser Asp Tyr Ser Ile Tyr Leu Glu Lys
1               5                   10                  15

Glu Ala Ala Gln Glu Phe Val Asn Trp Leu Leu Ala Gly Gly Pro Ser
            20                  25                  30

Ser Gly Ala Pro Pro Pro Ser Lys
        35                  40

<210> SEQ ID NO 11
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 11

Tyr Xaa Glu Gly Thr Phe Thr Ser Asp Tyr Ser Ile Tyr Leu Glu Lys
1               5                   10                  15

Glu Ala Gln Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 12
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (16)..(16)
<223> OTHER INFORMATION: Xaa is Aib.

<400> SEQUENCE: 12

Tyr Xaa Glu Gly Thr Phe Thr Ser Asp Tyr Ser Ile Tyr Leu Glu Xaa
1               5                   10                  15

Glu Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 13
<211> LENGTH: 40
```

```
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 13

Tyr Xaa Glu Gly Thr Phe Thr Ser Asp Tyr Ser Ile Tyr Leu Glu Lys
1               5                   10                  15

Ile Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 14
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 14

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser Lys
        35                  40

<210> SEQ ID NO 15
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 15

Tyr Xaa Glu Gly Thr Phe Thr Ser Asp Tyr Ser Ile Tyr Leu Glu Lys
1               5                   10                  15

Ile Ala Gln Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 16
<211> LENGTH: 40
<212> TYPE: PRT
<213> ORGANISM: Artificial Sequence
<220> FEATURE:
<221> NAME/KEY: VARIANT
```

```
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 16

Tyr Xaa Glu Gly Thr Phe Thr Ser Asp Tyr Ser Ile Tyr Leu Glu Lys
1               5                   10                  15

Glu Xaa Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 17
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (19)..(19)
<223> OTHER INFORMATION: Xaa is Aib.

<400> SEQUENCE: 17

Tyr Xaa Glu Gly Thr Phe Thr Ser Asp Tyr Ser Ile Tyr Leu Glu Lys
1               5                   10                  15

Glu Ala Xaa Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 18
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (16)..(16)
<223> OTHER INFORMATION: Xaa is Aib.

<400> SEQUENCE: 18

Tyr Xaa Glu Gly Thr Phe Thr Ser Asp Tyr Ser Ile Tyr Leu Glu Xaa
1               5                   10                  15

Ile Ala Ala Gln Glu Phe Val Asn Trp Leu Leu Ala Gly Gly Pro Ser
            20                  25                  30

Ser Gly Ala Pro Pro Pro Ser Lys
        35                  40
```

```
<210> SEQ ID NO 19
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 19

Tyr Xaa Glu Gly Thr Phe Thr Ser Asp Tyr Ser Ile Tyr Leu Asp Lys
1               5                   10                  15

Glu Ala Ala Lys Glu Phe Val Asn Trp Leu Leu Ala Gly Gly Pro Ser
                20                  25                  30

Ser Gly Ala Pro Pro Pro Ser Lys
        35                  40

<210> SEQ ID NO 20
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 20

Tyr Xaa Glu Gly Thr Phe Thr Ser Asp Tyr Ser Ile Tyr Leu Asp Lys
1               5                   10                  15

Ile Ala Ala Gln Glu Phe Val Asn Trp Leu Leu Ala Gly Gly Pro Ser
                20                  25                  30

Ser Gly Ala Pro Pro Pro Ser Lys
        35                  40

<210> SEQ ID NO 21
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 21

Tyr Xaa Glu Gly Thr Phe Thr Ser Asp Tyr Ser Ile Tyr Leu Asp Lys
1               5                   10                  15

Ile Ala Ala Gln Glu Phe Val Gln Trp Leu Leu Ala Gly Gly Pro Ser
                20                  25                  30

Ser Gly Ala Pro Pro Pro Ser Lys
        35                  40

<210> SEQ ID NO 22
<211> LENGTH: 40
```

```
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (16)..(16)
<223> OTHER INFORMATION: Xaa is Aib.

<400> SEQUENCE: 22

Tyr Xaa Glu Gly Thr Phe Thr Ser Asp Tyr Ser Ile Tyr Leu Asp Xaa
1               5                   10                  15

Ile Ala Ala Gln Glu Phe Val Gln Trp Leu Leu Ala Gly Gly Pro Ser
            20                  25                  30

Ser Gly Ala Pro Pro Pro Ser Lys
        35                  40

<210> SEQ ID NO 23
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 23

Tyr Xaa Glu Gly Thr Phe Thr Ser Asp Tyr Ser Ile Tyr Leu Glu Lys
1               5                   10                  15

Glu Ala Ala Lys Glu Phe Val Asn Trp Leu Leu Ala Gln Lys Pro Ser
            20                  25                  30

Ser Gly Ala Pro Pro Pro Ser Lys
        35                  40

<210> SEQ ID NO 24
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 24

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Leu Ala Gln Lys Pro Ser
            20                  25                  30

Ser Gly Ala Pro Pro Pro Ser Lys
        35                  40

<210> SEQ ID NO 25
<211> LENGTH: 40
```

```
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 25

Tyr Xaa Glu Gly Thr Phe Thr Ser Asp Tyr Ser Ile Tyr Leu Glu Lys
1               5                   10                  15

Glu Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 26
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 26

Tyr Xaa Glu Gly Thr Phe Thr Ser Asp Tyr Ser Ile Tyr Leu Glu Lys
1               5                   10                  15

Glu Ala Ala Lys Glu Phe Val Asn Trp Leu Leu Ala Gly Lys Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 27

Tyr Xaa Glu Gly Thr Phe Thr Ser Asp Tyr Ser Ile Tyr Leu Glu Lys
1               5                   10                  15

Glu Ala Ala Lys Glu Phe Val Asn Trp Leu Leu Ala Gly Gly Pro Ser
            20                  25                  30

Ser Gly Ala Pro Pro Pro Ser
        35

<210> SEQ ID NO 28
<211> LENGTH: 40
<212> TYPE: PRT
<213> ORGANISM: Artificial Sequence
<220> FEATURE:
<221> NAME/KEY: VARIANT
```

```
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 28

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser Lys
        35                  40

<210> SEQ ID NO 29
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 29

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Leu Ala Gly Lys Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 30

Tyr Xaa Glu Gly Thr Phe Thr Ser Asp Tyr Ser Ile Tyr Leu Glu Lys
1               5                   10                  15

Ile Ala Ala Lys Glu Phe Val Asn Trp Leu Leu Ala Gly Gly Pro Ser
            20                  25                  30

Ser Gly Ala Pro Pro Pro Ser
        35

<210> SEQ ID NO 31
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
```

-continued

```
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 31

Tyr Xaa Glu Gly Thr Phe Thr Ser Asp Tyr Ser Ile Tyr Leu Glu Lys
1               5                   10                  15

Glu Xaa Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 32
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 32

Tyr Xaa Glu Gly Thr Phe Thr Ser Asp Tyr Ser Ile Tyr Leu Glu Lys
1               5                   10                  15

Glu Xaa Ala Lys Glu Phe Val Asn Trp Leu Leu Ala Gly Lys Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 33

Tyr Xaa Glu Gly Thr Phe Thr Ser Asp Tyr Ser Ile Tyr Leu Glu Lys
1               5                   10                  15

Glu Xaa Ala Lys Glu Phe Val Asn Trp Leu Leu Ala Gly Gly Pro Ser
            20                  25                  30

Ser Gly Ala Pro Pro Pro Ser
        35

<210> SEQ ID NO 34
<211> LENGTH: 39
```

```
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 34

Tyr Xaa Glu Gly Thr Phe Thr Ser Asp Tyr Ser Ile Tyr Leu Glu Lys
1               5                   10                  15

Ile Ala Gln Gln Glu Phe Ile Gln Trp Leu Leu Ala Gly Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 35

Tyr Xaa Glu Gly Thr Phe Thr Ser Asp Tyr Ser Ile Tyr Leu Glu Lys
1               5                   10                  15

Ile Ala Gln Gln Glu Phe Ile Gln Trp Leu Leu Ala Gln Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 36

Tyr Xaa Glu Gly Thr Phe Thr Ser Asp Tyr Ser Ile Tyr Leu Glu Lys
1               5                   10                  15

Ile Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<221> NAME/KEY: VARIANT
```

```
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 37

Tyr Xaa Glu Gly Thr Phe Thr Ser Asp Tyr Ser Ile Tyr Leu Glu Gly
1               5                   10                  15

Ile Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 38

Tyr Xaa Glu Gly Thr Phe Thr Ser Asp Tyr Ser Ile Tyr Leu Glu Gly
1               5                   10                  15

Ile Ala Gln Gln Glu Phe Ile Gln Trp Leu Leu Ala Gly Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 39

Tyr Xaa Glu Gly Thr Phe Thr Ser Asp Tyr Ser Ile Tyr Leu Glu Lys
1               5                   10                  15

Ile Xaa Gln Gln Glu Phe Ile Gln Trp Leu Leu Ala Gly Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<221> NAME/KEY: VARIANT
```

```
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 40

Tyr Xaa Glu Gly Thr Phe Thr Ser Asp Tyr Ser Ile Tyr Leu Glu Lys
1               5                   10                  15

Gln Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 41

Tyr Xaa Glu Gly Thr Phe Thr Ser Asp Tyr Ser Ile Tyr Leu Glu Lys
1               5                   10                  15

Glu Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 42

Tyr Xaa Glu Gly Thr Phe Thr Ser Asp Tyr Ser Ile Tyr Leu Glu Gly
1               5                   10                  15

Gln Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
```

-continued

```
<222> LOCATION: (2)..(2)
<223> OTHER INFORMATION: Xaa is Aib.

<400> SEQUENCE: 43

Tyr Xaa Glu Gly Thr Phe Thr Ser Asp Tyr Ser Ile Tyr Leu Glu Glu
1               5                   10                  15

Glu Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 44

Tyr Xaa Glu Gly Thr Phe Thr Ser Asp Tyr Ser Ile Tyr Leu Glu Gly
1               5                   10                  15

Glu Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 45

Tyr Xaa Glu Gly Thr Phe Thr Ser Asp Tyr Ser Ile Tyr Leu Glu Glu
1               5                   10                  15

Ile Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 46
```

```
Tyr Xaa Glu Gly Thr Phe Thr Ser Asp Tyr Ser Ile Tyr Leu Glu Glu
1               5                   10                  15

Gln Ala Ala Gln Glu Phe Ile Gln Trp Leu Leu Ala Gly Gly Pro Ser
            20                  25                  30

Ser Gly Ala Pro Pro Pro Ser
        35

<210> SEQ ID NO 47
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 47

Tyr Xaa Glu Gly Thr Phe Thr Ser Asp Tyr Ser Ile Tyr Leu Glu Lys
1               5                   10                  15

Ile Ala Ala Gln Glu Phe Ile Gln Trp Leu Leu Ala Gly Gly Pro Ser
            20                  25                  30

Ser Gly Ala Pro Pro Pro Ser Lys
        35                  40

<210> SEQ ID NO 48
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 48

Tyr Xaa Glu Gly Thr Phe Thr Ser Asp Tyr Ser Ile Tyr Leu Glu Lys
1               5                   10                  15

Ile Ala Ala Gln Glu Phe Ile Asn Trp Leu Leu Ala Gly Gly Pro Ser
            20                  25                  30

Ser Gly Ala Pro Pro Pro Ser
        35

<210> SEQ ID NO 49
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 49

Tyr Xaa Glu Gly Thr Phe Thr Ser Asp Tyr Ser Ile Tyr Leu Glu Lys
1               5                   10                  15
```

```
Ile Ala Ala Lys Glu Phe Ile Asn Trp Leu Leu Ala Gly Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 50

Tyr Xaa Glu Gly Thr Phe Thr Ser Asp Tyr Ser Ile Tyr Leu Glu Lys
1               5                   10                  15

Ile Ala Ala Lys Glu Phe Val Asn Trp Leu Leu Ala Gly Lys Pro Ser
            20                  25                  30

Ser Gly Ala Pro Pro Pro Ser
        35

<210> SEQ ID NO 51
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 51

Tyr Xaa Glu Gly Thr Phe Thr Ser Asp Tyr Ser Ile Tyr Leu Glu Lys
1               5                   10                  15

Ile Ala Ala Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 52
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 52

Tyr Xaa Glu Gly Thr Phe Thr Ser Asp Tyr Ser Ile Tyr Leu Glu Lys
1               5                   10                  15

Ile Ala Ala Gln Glu Phe Ile Asn Trp Leu Leu Ala Gly Lys Pro Ser
            20                  25                  30

Ser Gly Ala Pro Pro Pro Ser
```

35

```
<210> SEQ ID NO 53
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 53

Tyr Xaa Glu Gly Thr Phe Thr Ser Asp Tyr Ser Ile Tyr Leu Glu Lys
1               5                   10                  15

Ile Ala Ala Gln Glu Phe Ile Asn Trp Leu Leu Ala Gly Gly Pro Ser
            20                  25                  30

Ser Gly Ala Pro Pro Pro Ser Lys
        35                  40

<210> SEQ ID NO 54
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 54

Tyr Xaa Glu Gly Thr Phe Thr Ser Asp Tyr Ser Ile Tyr Leu Glu Lys
1               5                   10                  15

Ile Ala Gln Lys Glu Phe Val Asn Trp Leu Leu Ala Gly Gly Pro Ser
            20                  25                  30

Ser Gly Ala Pro Pro Pro Ser
        35

<210> SEQ ID NO 55
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 55

Tyr Xaa Glu Gly Thr Phe Thr Ser Asp Tyr Ser Ile Tyr Leu Glu Lys
1               5                   10                  15

Ile Ala Gln Lys Glu Phe Val Asn Trp Leu Leu Ala Gly Lys Pro Ser
            20                  25                  30

Ser Gly Ala Pro Pro Pro Ser
        35

<210> SEQ ID NO 56
```

```
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 56

Tyr Xaa Glu Gly Thr Phe Thr Ser Asp Tyr Ser Ile Tyr Leu Glu Lys
1               5                   10                  15

Ile Ala Gln Lys Glu Phe Val Asn Trp Leu Leu Ala Gly Gly Pro Ser
            20                  25                  30

Ser Gly Ala Pro Pro Pro Ser Lys
        35                  40

<210> SEQ ID NO 57
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 57

Tyr Xaa Glu Gly Thr Phe Thr Ser Asp Tyr Ser Ile Tyr Leu Glu Lys
1               5                   10                  15

Glu Xaa Ala Lys Glu Phe Ile Asn Trp Leu Leu Ala Gly Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 58

Tyr Xaa Glu Gly Thr Phe Thr Ser Asp Tyr Ser Ile Tyr Leu Glu Lys
1               5                   10                  15

Glu Xaa Ala Lys Glu Phe Ile Asn Trp Leu Leu Ala Gly Lys Pro Ser
            20                  25                  30

Ser Gly Ala Pro Pro Pro Ser
```

-continued

35

```
<210> SEQ ID NO 59
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
<220> FEATURE:
<221> NAME/KEY: VARIANT
<222> LOCATION: (18)..(18)
<223> OTHER INFORMATION: Xaa is Aib.

<400> SEQUENCE: 59

Tyr Xaa Glu Gly Thr Phe Thr Ser Asp Tyr Ser Ile Tyr Leu Glu Lys
1               5                   10                  15

Glu Xaa Ala Lys Glu Phe Ile Asn Trp Leu Leu Ala Gly Gly Pro Ser
            20                  25                  30

Ser Gly Ala Pro Pro Pro Ser Lys
        35                  40

<210> SEQ ID NO 60
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 60

Tyr Xaa Glu Gly Thr Phe Thr Ser Asp Tyr Ser Ile Tyr Leu Asp Lys
1               5                   10                  15

Ile Ala Ala Lys Glu Phe Val Asn Trp Leu Leu Ala Gly Gly Pro Ser
            20                  25                  30

Ser Gly Ala Pro Pro Pro Ser
        35

<210> SEQ ID NO 61
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 61

Tyr Xaa Glu Gly Thr Phe Thr Ser Asp Tyr Ser Ile Tyr Leu Asp Lys
1               5                   10                  15

Ile Ala Ala Gln Glu Phe Val Asn Trp Leu Leu Ala Gly Lys Pro Ser
            20                  25                  30

Ser Gly Ala Pro Pro Pro Ser
```

```
                 35

<210> SEQ ID NO 62
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 62

Tyr Xaa Glu Gly Thr Phe Thr Ser Asp Tyr Ser Ile Tyr Leu Asp Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser Lys
        35                  40

<210> SEQ ID NO 63
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 63

Tyr Xaa Glu Gly Thr Phe Thr Ser Asp Tyr Ser Ile Tyr Leu Glu Lys
1               5                   10                  15

Glu Ala Ala Lys Glu Phe Ile Asn Trp Leu Leu Ala Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 64

Tyr Xaa Glu Gly Thr Phe Thr Ser Asp Tyr Ser Ile Tyr Leu Glu Lys
1               5                   10                  15

Glu Ala Ala Lys Glu Phe Val Gln Trp Leu Leu Ala Gly Gly Pro Ser
            20                  25                  30

Ser Gly Ala Pro Pro Pro Ser
        35

<210> SEQ ID NO 65
```

```
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 65

Tyr Xaa Glu Gly Thr Phe Thr Ser Asp Tyr Ser Ile Tyr Leu Glu Lys
1               5                   10                  15

Glu Ala Ala Lys Glu Phe Ile Gln Trp Leu Leu Ala Gly Gly Pro Ser
            20                  25                  30

Ser Gly Ala Pro Pro Pro Ser
        35

<210> SEQ ID NO 66
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 66

Tyr Xaa Glu Gly Thr Phe Thr Ser Asp Tyr Ser Ile Tyr Leu Glu Lys
1               5                   10                  15

Glu Ala Ala Lys Glu Phe Val Ala Trp Leu Leu Ala Gly Gly Pro Ser
            20                  25                  30

Ser Gly Ala Pro Pro Pro Ser
        35

<210> SEQ ID NO 67
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 67

Tyr Xaa Glu Gly Thr Phe Thr Ser Asp Tyr Ser Ile Tyr Leu Glu Lys
1               5                   10                  15

Glu Ala Ala Lys Glu Phe Ile Ala Trp Leu Leu Ala Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial Sequence
<220> FEATURE:
```

```
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 68

Tyr Xaa Glu Gly Thr Phe Thr Ser Asp Val Ser Ile Tyr Leu Glu Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 69

Tyr Xaa Glu Gly Thr Phe Thr Ser Asp Val Ser Ile Tyr Leu Asp Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 70

Tyr Xaa Glu Gly Thr Phe Thr Ser Asp Tyr Ser Ile Tyr Leu Glu Glu
1               5                   10                  15

Ile Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
```

-continued

```
<221> NAME/KEY: VARIANT
<222> LOCATION: (2)..(2)
<223> OTHER INFORMATION: Xaa is Aib.

<400> SEQUENCE: 71

Tyr Xaa Glu Gly Thr Phe Thr Ser Asp Tyr Ser Ile Tyr Leu Glu Glu
1               5                   10                  15

Glu Ala Ala Lys Glu Phe Val Asn Trp Leu Leu Ala Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 72

Tyr Xaa Glu Gly Thr Phe Thr Ser Asp Tyr Ser Ile Tyr Leu Glu Glu
1               5                   10                  15

Ile Ala Ala Lys Glu Phe Val Asn Trp Leu Leu Ala Gly Gly Pro Ser
            20                  25                  30

Ser Gly Ala Pro Pro Pro Ser
        35

<210> SEQ ID NO 73
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 73

Tyr Xaa Glu Gly Thr Phe Thr Ser Asp Tyr Ser Ile Tyr Leu Glu Glu
1               5                   10                  15

Glu Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 74
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.
```

```
<400> SEQUENCE: 74

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Leu Ala Gly Gly Pro Ser
            20                  25                  30

Ser Gly Ala Pro Pro Pro Ser Lys
        35                  40

<210> SEQ ID NO 75
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 75

Tyr Xaa Glu Gly Thr Phe Thr Ser Asp Tyr Ser Ile Tyr Leu Glu Lys
1               5                   10                  15

Ile Ala Ala Lys Glu Phe Val Asn Trp Leu Leu Ala Gly Gly Pro Ser
            20                  25                  30

Ser Gly Ala Pro Pro Pro Ser
        35

<210> SEQ ID NO 76
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 76

Tyr Xaa Glu Gly Thr Phe Thr Ser Asp Tyr Ser Ile Tyr Leu Glu Lys
1               5                   10                  15

Glu Ala Ala Lys Glu Phe Ile Asn Trp Leu Leu Ala Gly Gly Pro Ser
            20                  25                  30

Ser Gly Ala Pro Pro Pro Ser Lys
        35                  40

<210> SEQ ID NO 77
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 77

Tyr Xaa Glu Gly Thr Phe Thr Ser Asp Tyr Ser Ile Tyr Leu Glu Glu
1               5                   10                  15
```

```
Ile Ala Ala Gln Glu Phe Ile Asn Trp Leu Leu Ala Gly Gly Pro Ser
            20                  25                  30

Ser Gly Ala Pro Pro Pro Ser Lys
        35                  40
```

<210> SEQ ID NO 78
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 78

```
Tyr Xaa Glu Gly Thr Phe Thr Ser Asp Tyr Ser Ile Tyr Leu Glu Lys
1               5                   10                  15

Ile Ala Ala Gln Glu Phe Val Gln Trp Leu Leu Ala Gly Gly Pro Ser
            20                  25                  30

Ser Gly Ala Pro Pro Pro Ser
        35
```

<210> SEQ ID NO 79
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 79

```
Tyr Xaa Glu Gly Thr Phe Thr Ser Asp Tyr Ser Ile Tyr Leu Glu Lys
1               5                   10                  15

Ile Ala Ala Gln Glu Phe Val Gln Trp Leu Ile Ala Gly Gly Pro Ser
            20                  25                  30

Ser Gly Ala Pro Pro Pro Ser
        35
```

<210> SEQ ID NO 80
<211> LENGTH: 39
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 80

```
Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Ile Ala Gly Gly Pro Ser
            20                  25                  30
```

```
Ser Gly Ala Pro Pro Pro Ser
        35

<210> SEQ ID NO 81
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 81

Tyr Xaa Glu Gly Thr Phe Thr Ser Asp Tyr Ser Ile Tyr Leu Glu Lys
1               5                   10                  15

Ile Ala Ala Gln Glu Phe Val Gln Trp Leu Leu Ala Gly Gly Pro Ser
            20                  25                  30

Ser Gly Ala Pro Pro Pro Ser Lys
        35                  40

<210> SEQ ID NO 82
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 82

Tyr Xaa Glu Gly Thr Phe Thr Ser Asp Tyr Ser Ile Tyr Leu Glu Lys
1               5                   10                  15

Ile Ala Ala Gln Glu Phe Val Gln Trp Leu Ile Ala Gly Gly Pro Ser
            20                  25                  30

Ser Gly Ala Pro Pro Pro Ser Lys
        35                  40

<210> SEQ ID NO 83
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (2)..(2)
<223> OTHER INFORMATION: Xaa is Aib.

<400> SEQUENCE: 83

Tyr Xaa Glu Gly Thr Phe Thr Ser Asp Tyr Ser Ile Tyr Leu Glu Lys
1               5                   10                  15

Ile Ala Ala Gln Glu Phe Val Asn Trp Leu Ile Ala Gly Gly Pro Ser
            20                  25                  30

Ser Gly Ala Pro Pro Pro Ser Lys
        35                  40
```

```
<210> SEQ ID NO 84
<211> LENGTH: 40
<212> TYPE: PRT
<213> ORGANISM: Artificial Sequence
<220> FEATURE:
<221> NAME/KEY: VARIANT
<222> LOCATION:
<223> OTHER INFORMATION: GLP-1 analog
<220> FEATURE:
<221> NAME/KEY: VARIANT
<222> LOCATION: (1)..(1)
<223> OTHER INFORMATION: Xaa can be any natural amino acid, or unnatural
      amino acid, or peptide fragment consisting of natural/unnatural
      amino acid; preferable Tyr or His.
<220> FEATURE:
<221> NAME/KEY: VARIANT
<222> LOCATION: (2)..(2)
<223> OTHER INFORMATION: Xaa can be any natural amino acid, or unnatural
      amino acid, or peptide fragment consisting of natural/unnatural
      amino acid; preferable Aib or D-Ala.
<220> FEATURE:
<221> NAME/KEY: VARIANT
<222> LOCATION: (10)..(10)
<223> OTHER INFORMATION: Xaa can be any natural amino acid, or unnatural
      amino acid, or peptide fragment consisting of natural/unnatural
      amino acid; preferable Val or Tyr.
<220> FEATURE:
<221> NAME/KEY: VARIANT
<222> LOCATION: (12)..(12)
<223> OTHER INFORMATION: Xaa can be any natural amino acid, or unnatural
      amino acid, or peptide fragment consisting of natural/unnatural
      amino acid; preferable Ser or Ile.
<220> FEATURE:
<221> NAME/KEY: VARIANT
<222> LOCATION: (15)..(15)
<223> OTHER INFORMATION: Xaa can be any natural amino acid, or unnatural
      amino acid, or peptide fragment consisting of natural/unnatural
      amino acid; preferable Asp or Glu.
<220> FEATURE:
<221> NAME/KEY: VARIANT
<222> LOCATION: (16)..(16)
<223> OTHER INFORMATION: Xaa can be any natural amino acid, or unnatural
      amino acid, or peptide fragment consisting of natural/unnatural
      amino acid; preferable Glu, Gly, Lys or Aib.
<220> FEATURE:
<221> NAME/KEY: VARIANT
<222> LOCATION: (17)..(17)
<223> OTHER INFORMATION: Xaa can be any natural amino acid, or unnatural
      amino acid, or peptide fragment consisting of natural/unnatural
      amino acid; preferable Glu, Ile or Gln.
<220> FEATURE:
<221> NAME/KEY: VARIANT
<222> LOCATION: (18)..(18)
<223> OTHER INFORMATION: Xaa can be any natural amino acid, or unnatural
      amino acid, or peptide fragment consisting of natural/unnatural
      amino acid; preferable Ala, Aib or His.
<220> FEATURE:
<221> NAME/KEY: VARIANT
<222> LOCATION: (19)..(19)
<223> OTHER INFORMATION: Xaa can be any natural amino acid, or unnatural
      amino acid, or peptide fragment consisting of natural/unnatural
      amino acid; preferable Ala, Aib or Gln.
<220> FEATURE:
<221> NAME/KEY: VARIANT
<222> LOCATION: (20)..(20)
<223> OTHER INFORMATION: Xaa can be any natural amino acid, or unnatural
      amino acid, or peptide fragment consisting of natural/unnatural
      amino acid; preferable Gln, Glu, Lys or Y1.
<220> FEATURE:
<221> NAME/KEY: VARIANT
<222> LOCATION: (23)..(23)
<223> OTHER INFORMATION: Xaa can be any natural amino acid, or unnatural
      amino acid, or peptide fragment consisting of natural/unnatural
      amino acid; preferable Ile or Val.
<220> FEATURE:
<221> NAME/KEY: VARIANT
<222> LOCATION: (24)..(24)
<223> OTHER INFORMATION: Xaa can be any natural amino acid, or unnatural
      amino acid, or peptide fragment consisting of natural/unnatural
```

-continued

```
       amino acid; preferable Ala, Asn or Gln.
<220> FEATURE:
<221> NAME/KEY: VARIANT
<222> LOCATION: (27)..(27)
<223> OTHER INFORMATION: Xaa can be any natural amino acid, or unnatural
       amino acid, or peptide fragment consisting of natural/unnatural
       amino acid; preferable Val or Leu.
<220> FEATURE:
<221> NAME/KEY: VARIANT
<222> LOCATION: (28)..(28)
<223> OTHER INFORMATION: Xaa can be any natural amino acid, or unnatural
       amino acid, or peptide fragment consisting of natural/unnatural
       amino acid; preferable Arg or Ala.
<220> FEATURE:
<221> NAME/KEY: VARIANT
<222> LOCATION: (29)..(29)
<223> OTHER INFORMATION: Xaa can be any natural amino acid, or unnatural
       amino acid, or peptide fragment consisting of natural/unnatural
       amino acid; preferable Gly or Gln.
<220> FEATURE:
<221> NAME/KEY: VARIANT
<222> LOCATION: (30)..(30)
<223> OTHER INFORMATION: Xaa can be any natural amino acid, or unnatural
       amino acid, or peptide fragment consisting of natural/unnatural
       amino acid; preferable Gly, Lys or Y1.
<220> FEATURE:
<221> NAME/KEY: VARIANT
<222> LOCATION: (40)..(40)
<223> OTHER INFORMATION: Xaa can be any natural amino acid, or unnatural
       amino acid, or peptide fragment consisting of natural/unnatural
       amino acid; or Xaa can be absent; preferable Lys or Y1 or absent.

<400> SEQUENCE: 84

Xaa Xaa Glu Gly Thr Phe Thr Ser Asp Xaa Ser Xaa Tyr Leu Xaa Xaa
1               5                   10              15

Xaa Xaa Xaa Xaa Glu Phe Xaa Xaa Trp Leu Xaa Xaa Xaa Xaa Pro Ser
            20                  25                  30

Ser Gly Ala Pro Pro Pro Ser Xaa
        35                  40
```

1

MULTI-RECEPTOR AGONIST AND MEDICAL USE THEREOF

CROSS-REFERENCE TO RELATED APPLICATION

This application is a Section 371 of International Application No. PCT/CN2020/084247 filed Apr. 10, 2020, which was published in the Chinese language Oct. 15, 2020, under International Publication No. WO 2020/084247 A1, which claims priority to Chinese Patent Application No. 201910290162.6 filed Apr. 11, 2019 and Chinese Patent Application No. 201911120906.6 filed Nov. 15, 2019, the disclosures of which are incorporated herein by reference in their entireties.

REFERENCE TO SEQUENCE LISTING SUBMITTED ELECTRONICALLY SECTION

This application contains a sequence listing, which is submitted electronically via EFS-Web as an ASCII formatted sequence listing with a file name "065825_127US1 Sequence Listing" and a creation date of Oct. 21, 2021 and having a size of 48 kb. The sequence listing submitted via EFS-Web is part of the specification and is herein incorporated by reference in its entirety.

FIELD OF THE INVENTION

The invention belongs to the field of biomedicine, and specifically relates to an agonist having agonistic effect on both human glucagon-like peptide 1 (GLP-1) receptor and human glucose-dependent insulinotropic polypeptide (GIP) receptor, and the use thereof for the treatment of metabolic diseases such as non-insulin-dependent diabetes, insulin-dependent diabetes and obesity-related diseases.

BACKGROUND OF THE INVENTION

Diabetes, a metabolic disease, is dysregulation of in vivo glucose, protein, and lipid metabolism due to insufficient insulin secretion in vivo. Diabetes is mainly classified into insulin-dependent diabetes (type 1 diabetes) and non-insulin-dependent diabetes (type 2 diabetes) based on the difference of its pathological mechanism. Among them, 90-95% of diabetic patients worldwide have non-insulin-dependent diabetes. Non-insulin-dependent diabetes is a long-term, chronic metabolic disease caused by impaired pancreatic β-cell function and long-term insulin resistance, characterized in the deficiency of insulin levels in vivo and the high blood glucose concentration in plasma. Studies have shown that non-insulin-dependent diabetes is associated with a variety of high-risk diseases in patients, and it often leads to cardiovascular disease, kidney failure, blindness, amputation and other diseases.

One of the main causes of non-insulin-dependent diabetes is obesity. Obesity is defined as excessive or abnormal fat accumulation in the body that damages human health. According to a person's body mass index (BMI), obesity can also be defined as a person's BMI index greater than or equal to 30 kg/m$^2$. The occurrence of obesity will significantly increase the risk of cardiovascular disease, diabetes, musculoskeletal diseases and certain cancers. In addition, an increase in the human body mass index will also increase the risk of certain non-infectious diseases.

Due to the huge number of patients and the consequently significant economic burden caused by diabetes and com-plications thereof, the development of safe and effective agents for the treatment of diabetes has always been one of the focus areas for many research institutions and pharmaceutical companies. At present, the approved diabetes agents mainly include chemically synthesized small-molecule oral hypoglycemic agents, such as biguanides, sulfonyls, insulin sensitizing agents, α-glycosides, and injectable hypoglycemic agents such as recombinant insulins and derivatives thereof produced by biosynthesis. Although the above-mentioned agents can effectively control the blood glucose level in the plasma of diabetic patients clinically, adverse reactions such as weight gain is often accompanied by the long-term use of these agents, which in turn leads to an increase in the risk of potential cardiovascular disease and a decrease in patient compliance. Considering the potential pathological relationship between diabetes and obesity, and the potential risk of complications caused by obesity, it is significantly important in many ways to develop agents that can both effectively control the blood glucose and appropriately reduce the body weight of diabetic patients, such as for purposes of effective treatment of diabetes and also for the reduction of the risk of potential complications. It is therefore a more excellent clinical research direction.

Glucagon-like peptide 1 (GLP-1) is a gastrointestinal regulatory polypeptide comprising 30 or 31 amino acid residues. The secretion of GLP-1 is mainly regulated by L-cells in the small intestine, in response to the absorption of nutrients and the fluctuating blood glucose levels in vivo. After food intake, the L-cells of the small intestine secrete a large amount of GLP-1 to enhance the endocrine function of the pancreas. GLP-1 polypeptide mainly achieves its in vivo physiological functions of controlling blood glucose and reducing appetite by activating GLP-1 receptors distributed on the surface of cell membranes. The main mechanism by which GLP-1 controls blood glucose levels in vivo is to activate its GLP-1 receptors distributed in pancreatic β cells to promote insulin biosynthesis and secretion. At the same time, when the in vivo blood glucose level is high, GLP-1 polypeptide can inhibit the secretion of glucagon, gastric emptying and food intake, and can also promote the in vivo degradation of glucose through specific nervous system effects. It is worth noting that the physiological function of GLP-1 polypeptide to promote insulin secretion is highly controlled by plasma glucose concentration. Therefore, GLP-1 polypeptide does not cause severe and long-lasting hypoglycemia compared to other therapeutic agents for the treatment of diabetes. In addition, it has been reported in the literature that GLP-1 polypeptide and analogs thereof can directly promote the growth, differentiation and proliferation of β cells in experimental animals, indicating the physiological effect of GLP-1 polypeptide and analogs thereof on protecting pancreatic islets and delaying the progression of diabetes, thereby inhibiting R cell apoptosis. GLP-1 polypeptide also has the potential to inhibit the secretion of gastrin and gastric acid stimulated by food intaking. Such characteristics mean that GLP-1 polypeptide also has a physiological role in preventing peptic ulcers. GLP-1 polypeptide can also activate its GLP-1 receptors distributed in the central nervous system (the brain) to enhance satiety, reduce food intake and achieve the physiological effect of maintaining or reducing the body weight. Therefore, due to the extensive action mechanisms and physiological functions of GLP-1 polypeptide and analogs thereof, GLP-1 polypeptide is an ideal agent for the treatment of non-insulin-dependent diabetes and obesity diabetes.

The physiological functions of GLP-1 polypeptide in controlling the blood glucose and reducing the body weight have brought hope for the treatment of non-insulin-dependent diabetes/obesity diabetes. However, natural human GLP-1 has poor druggability, because it is susceptible to degradation by dipeptide-based peptidase-IV (DPP-IV) in vivo, so that its half-life in the human body is only 1-2 minutes. When faced with such difficulty, the pharmaceutical industry has constructed long-acting GLP-1 analogs and derivatives thereof by site-directed amino acid mutations at restriction site(s), fatty acid modification for the polypeptide backbone, and binding the GLP-1 polypeptide to various protein/polymers. The long-acting GLP-1 analogs that are available on the market and are widely used in clinical practice include exenatide (subcutaneous injection, bid.), liraglutide (subcutaneous injection, qd.), and dulaglutide and semaglutide (subcutaneous injection, qw.) and so on.

Clinically, the side effects of GLP-1 polypeptide and derivatives thereof are mainly manifested in nausea, vomiting and diarrhea caused by the gastrointestinal tract; in addition, it has been found that GLP-1 polypeptide and derivatives thereof can also cause heart racing in a subject, and under certain circumstances, they can increase the risk of pancreatitis in patients. Therefore, the dosage of GLP-1 polypeptide and derivatives thereof is limited due to the side effects caused by them, so they can not achieve a total blood glucose control and body weight loss in patients when used clinically.

Both Glucose-dependent insulinotropic polypeptide (GIP) and GLP-1 polypeptide belong to types of incretin, which play a key physiologically relevant role in the metabolism of blood glucose in vivo. GIP is mainly composed of 42 amino acid residues in vivo and is secreted by K cells present in the duodenum and adjacent to the jejunum, in response to the plasma level of glucose. GIP polypeptide exerts its physiological effects by binding to its GIP receptors distributed in pancreatic $\beta$ cells, adipose tissue and central nervous system. Similar to GLP-1 polypeptide, GIP polypeptide can stimulate pancreatic $\beta$ cells to secrete insulin, thereby reducing the blood glucose concentration in plasma, protecting pancreatic $\beta$ cells, and controlling glucose metabolism in vivo. In addition, the physiological functions of GIP polypeptide also include activating its GIP receptor in adipose tissue, thereby promoting fat metabolism. Interestingly, intracerebroventricular injection of GIP polypeptide in mice can reduce the food intake and body weight in the test animals, which seems to indicate that GIP polypeptide also has certain physiological functions in reducing body weight. Studies have shown that the incretin function of GIP polypeptide in patients with non-insulin-dependent diabetes is greatly reduced, which leads to the lack or loss of incretin effects in patients. Studies have shown that the inhibition of the GIP polypeptide observed in these diabetic patients will be greatly weakened, when the blood glucose level returns to normal.

Therefore, there is a clinical need for a method of treating non-insulin-dependent diabetes with GIP polypeptide, and a clinical need for a clinically effective hypoglycemic agent to restore the tolerance of non-insulin-dependent diabetic patients to GIP polypeptide, which is further combined with the incretin effect of the GIP polypeptide, so as to obtain a stronger clinical hypoglycemic effect. Therefore, when compared with many GLP-1 receptor agonist polypeptides in the art, the purpose of the present invention is to provide a derivative of GLP-1 analog, which has an agonist activity to the human GIP receptor, and has dual agonist effect on both human GLP-1 receptor and human GIP receptor. In addition, certain compounds of the present invention have a stronger effect on lowering the blood glucose and losing weight than GLP-1 receptor agonists in this field. Finally, certain compounds of the present invention have extremely high plasma stability and have pharmacokinetics properties that support the administration of subcutaneous injection in human for once per week.

SUMMARY OF THE INVENTION

The purpose of the present invention is to provide a GLP-1 analog with general formula (I), or a pharmaceutically acceptable salt form thereof:

$$X_1-X_2-Glu-Gly-Thr-Phe-Thr-Ser-Asp-X_{10}-Ser-X_{12}-Tyr- \tag{I}$$
$$Leu-X_{15}-X_{16}-X_{17}-X_{18}-X_{19}-X_{20}-Glu-Phe-X_{23}-X_{24}-Trp-Leu-$$
$$X_{27}-X_{28}-X_{29}-X_{30}-Pro-Ser-Ser-Gly-Ala-Pro-Pro-Pro-Ser-$$
$$X_{40}$$

wherein:

$X_1$, $X_2$, $X_{10}$, $X_{12}$, $X_{15}$, $X_{16}$, $X_{17}$, $X_{18}$, $X_{19}$, $X_{20}$, $X_{27}$, $X_{28}$, $X_{29}$ and $X_{30}$ are independently selected from any natural amino acid or unnatural amino acid or peptide fragment consisting of the same;

$X_{40}$ is selected from any natural amino acid or unnatural amino acid or peptide fragment consisting of the same, or $X_{40}$ is absent.

The present invention also relates to a technical solution, which involves a GLP-1 analog with general formula (I) or the pharmaceutically acceptable salt thereof, characterized in that the GLP-1 analog is modified at both ends thereof in the following way:

$$R_1-X_1-X_2-Glu-Gly-Thr-Phe-Thr-Ser-Asp-X_{10}-Ser-X_{12}- \tag{II}$$
$$Tyr-Leu-X_{15}-X_{16}-X_{17}-X_{18}-X_{19}-X_{20}-Glu-Phe-X_{23}-X_{24}-$$
$$Trp-Leu-X_{27}-X_{28}-X_{29}-X_{30}-Pro-Ser-Ser-Gly-Ala-Pro-$$
$$Pro-Pro-Ser-X_{40}-R_2$$

wherein:

$R_1$ is H, alkyl, acetyl, formyl, benzoyl, trifluoroacetyl or pGlu; $R_2$ is —$NH_2$ or —OH;

$X_1$, $X_2$, $X_{10}$, $X_{12}$, $X_{15}$, $X_{16}$, $X_{17}$, $X_{18}$, $X_{19}$, $X_{20}$, $X_{27}$, $X_{28}$, $X_{29}$ and $X_{30}$ are independently selected from any natural amino acid or unnatural amino acid or peptide fragment consisting of the same;

$X_{40}$ is selected from any natural amino acid or unnatural amino acid or peptide fragment consisting of the same, or $X_{40}$ is absent.

The present invention also relates to a preferred technical solution, which involves the GLP-1 analog with general formula (I) or the pharmaceutically acceptable salt thereof, the $X_1$ is selected from the amino acid residue Tyr or His; $X_2$ is selected from the amino acid residue Aib or D-Ala; $X_{10}$ is selected from the amino acid residue Val or Tyr; $X_{12}$ is selected from the amino acid residue Ser or Ile, $X_{15}$ is selected from the amino acid residue Asp or Glu; $X_{16}$ is selected from the amino acid residue Glu, Gly, Lys or Aib; $X_{17}$ is selected from the amino acid residue Glu, Ile or Gln; $X_{18}$ is selected from the amino acid residue Ala, Aib or His; $X_{19}$ is selected from the amino acid residue Ala, Aib or Gln; $X_{20}$ is selected from the amino acid residue Gln, Glu, Lys or Y1; $X_{23}$ is selected from the amino acid residue Ile or Val; $X_{24}$ is selected from the amino acid residue Ala, Asn or Gln;

$X_{27}$ is selected from the amino acid residue Val, Ile or Leu; $X_{28}$ is selected from the amino acid residue Arg or Ala; $X_{29}$ is selected from the amino acid residue Gly or Gln; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr or His; $X_2$ is selected from the amino acid residue Aib or D-Ala; $X_{10}$ is selected from the amino acid residue Val or Tyr; $X_{12}$ is selected from the amino acid residue Ser or Ile, $X_{15}$ is selected from the amino acid residue Asp or Glu; $X_{16}$ is selected from the amino acid residue Glu, Gly, Lys or Aib; $X_{17}$ is selected from the amino acid residue Glu, Ile or Gln; $X_{18}$ is selected from the amino acid residue Ala, Aib or His; $X_{19}$ is selected from the amino acid residue Ala, Aib or Gln; $X_{20}$ is selected from the amino acid residue Gln, Glu, Lys or Y1; $X_{23}$ is selected from the amino acid residue Ile or Val; $X_{24}$ is selected from the amino acid residue Ala, Asn or Gln; $X_{27}$ is selected from the amino acid residue Val, or Leu; $X_{28}$ is selected from the amino acid residue Arg or Ala; $X_{29}$ is selected from the amino acid residue Gly or Gln; $X_{30}$ is selected from the amino acid residue Gly, Lys or Y1; $X_{40}$ is selected from the amino acid residue Lys or Y1, or is absent; Y1 is Lys, Orn, Dap, Dab or Cys residue, in which a side chain is coupled to a substituent shown as formula of $\{[2$-$(2$-amino-ethoxy)-ethoxy]-acetyl$\}_a$-$(\gamma$-Glu$)_b$-CO—$(CH_2)_c$—COOH; wherein a is an integer between 1-3; b is an integer between 1-2; and c is an integer between 10-30.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Asp or Glu; $X_{16}$ is selected from the amino acid residue Lys or Aib; $X_{17}$ is selected from the amino acid residue Glu or Ile; $X_{18}$ is selected from the amino acid residue Ala or Aib; $X_{19}$ is selected from the amino acid residue Ala or Gln; $X_{20}$ is selected from the amino acid residue Gln, Lys, or Y1; $X_{23}$ is selected from the amino acid residue Val; $X_{24}$ is selected from the amino acid residue Asn or Gln; $X_{27}$ is selected from the amino acid residue Leu; $X_{28}$ is selected from the amino acid residue Ala; $X_{29}$ is selected from the amino acid residue Gly or Gln; $X_{30}$ is selected from the amino acid residue Gly, Lys or Y1; $X_{40}$ is selected from the amino acid residue Lys or Y1, or is absent; Y1 is Lys, Orn, Dap, Dab or Cys residue, in which a side chain is coupled to a substituent shown as formula of $\{[2$-$(2$-amino-ethoxy)-ethoxy]-acetyl$\}_a$-$(\gamma$-Glu$)_b$-CO—$(CH_2)_c$—COOH; wherein a is an integer between 1-3; b is an integer between 1-2; and c is an integer between 10-30.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Glu; $X_{18}$ is selected from the amino acid residue Ala or Aib; $X_{19}$ is selected from the amino acid residue Ala; $X_{20}$ is selected from the amino acid residue Gln, Lys or Y1; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Ile; $X_{18}$ is selected from the amino acid residue Ala or Aib; $X_{19}$ is selected from the amino acid residue Ala; $X_{20}$ is selected from the amino acid residue Gln, Lys or Y1; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Glu or Ile; $X_{18}$ is selected from the amino acid residue Ala; $X_{19}$ is selected from the amino acid residue Ala; $X_{20}$ is selected from the amino acid residue Gln, Lys or Y1; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Glu or Ile; $X_{18}$ is selected from the amino acid residue Aib; $X_{19}$ is selected from the amino acid residue Ala; $X_{20}$ is selected from the amino acid residue Gln, Lys or Y1; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Glu or Ile; $X_{18}$ is selected from the amino acid residue Ala or Aib; $X_{19}$ is selected from the amino acid residue Ala; $X_{20}$ selected from the amino acid residue Gln; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Glu or Ile; $X_{18}$ is selected from the amino acid residue Ala or Aib; $X_{19}$ is selected from the amino acid residue Ala; $X_{20}$ is selected from the amino acid residue Lys; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein the $X_1$ is selected from the amino acid residue Tyr; $X_2$ is selected from the amino acid residue Aib; $X_{10}$ is selected from the amino acid residue Tyr; $X_{12}$ is selected from the amino acid residue Ile, $X_{15}$ is selected from the amino acid residue Glu; $X_{16}$ is selected from the amino acid residue Lys; $X_{17}$ is selected from the amino acid residue Glu or Ile; $X_{18}$ is selected from the amino acid residue Ala or Aib; $X_{19}$ is selected from the amino acid residue Ala; $X_{20}$ is selected from Y1; $X_{23}$ is selected from the amino acid residue Val; $X_{24}$ is selected from the amino acid residue Asn; $X_{27}$ is selected from the amino acid residue Leu; $X_{28}$ is selected from the amino acid residue Ala; $X_{29}$ is selected from the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, wherein $X_1$ is the amino acid residue Tyr; $X_2$ is the amino acid residue Aib; $X_{10}$ is the amino acid residue Tyr; $X_{12}$ is the amino acid residue Ile; $X_{15}$ is the amino acid residue Glu; $X_{16}$ is the amino acid residue Lys; $X_{17}$ is selected from the amino acid residue Glu or Ile; $X_{18}$ is selected from the amino acid residue Ala or Aib; $X_{19}$ is the amino acid residue Ala; $X_{20}$ is Gln; $X_{23}$ is the amino acid residue Val; $X_{24}$ is the amino acid residue Asn; $X_{27}$ is the amino acid residue Leu; $X_{28}$ is the amino acid residue Ala; $X_{29}$ is the amino acid residue Gly; $X_{30}$ is selected from the amino acid residue Gly, Lys or Y1; $X_{40}$ is selected from the amino acid residue Lys or Y1, or is absent.

The present invention also relates to a preferred technical solution, which involves the GLP-1 analog with general formula (I) or the pharmaceutically acceptable salt thereof, and $X_{20}$, $X_{30}$ and $X_{40}$ are each independently selected from Y1.

Among them, Y1 is Lys, Orn, Dap, Dab or Cys residue, in which a side chain is coupled to a substituent shown as formula of $\{[2\text{-}(2\text{-amino-ethoxy})\text{-ethoxy}]\text{-acetyl}\}_a\text{-}(\text{y-Glu})_b\text{-CO}—(CH_2)_c—COOH$; a is an integer between 1-3; b is an integer between 1-2; and c is an integer between 10-30.

The present invention also relates to a preferred technical solution, which involves the GLP-1 analog with general formula (I) or the pharmaceutically acceptable salt thereof, in the definition of Y1, a is 2, b is 1 or 2, and c is 16-20.

The present invention also relates to a preferred technical solution, which involves the GLP-1 analog with general formula (I) or the pharmaceutically acceptable salt thereof, in the definition of Y1, a is 2, b is 1 or 2, and c is 16, 18 or 20.

The present invention also relates to a preferred technical solution, which involves the GLP-1 analog with general formula (I) or the pharmaceutically acceptable salt thereof, $X_{40}$ is selected from Y1;

Y1 is Lys residue, in which a side chain is coupled to a substituent shown as formula of $\{[2\text{-}(2\text{-amino-ethoxy})\text{-ethoxy}]\text{-acetyl}\}_a\text{-}(\text{y-Glu})_b\text{-CO}—(CH_2)_c—COOH$;

a is 2;

b is 1 or 2;

c is 16 or 18.

The present invention also relates to a preferred technical solution, which involves the GLP-1 analog with general formula (I) or the pharmaceutically acceptable salt thereof, Y1 is covalently linked to a fatty acid via the side chain amino group of Lys through forming an amide bond.

The present invention also relates to a preferred technical solution, which involves the GLP-1 analog with general formula (I) or the pharmaceutically acceptable salt thereof, Y1 is K (-OEG-OEG-yGlu-C18-OH) or K (-OEG-OEG-yGlu-C20-OH) which is shown as the chemical formula comprising the following structure:

-continued

The present invention also relates to a preferred technical solution, which involves the GLP-1 analog with general formula (I) or the pharmaceutically acceptable salt thereof, wherein the -OEG-OEG-yGlu-C18-OH or -OEG-OEG-yGlu-C20-OH group which is shown as the chemical formula comprising the following structure:

The present invention also relates to a preferred technical solution, which involves the GLP-1 analog with general formula (I) or the pharmaceutically acceptable salt thereof, Y1 is covalently linked to a fatty acid via the ε amino group of the C-terminal Lys through an amide bond, and the α amino group of the C-terminal Lys is linked to the peptide chain.

The present invention also relates to a preferred technical solution, which involves the GLP-1 analog with general formula (I) or the pharmaceutically acceptable salt thereof, characterized in that it is selected from the following compounds of numbers 1-83:

| Compound number | sequence |
| --- | --- |
| 1 | H-HAibEGTFTSDVSSYLEEEAAKEFIAWLVRGGPSSGAPPPSK-NH$_2$ |
| 2 | H-YAibEGTFTSDVSSYLEEEAAKEFIAWLVRGGPSSGAPPPSK-NH$_2$ |
| 3 | H-YAibEGTFTSDVSSYLEEHQKEFIAWLVRGGPSSGAPPPSK-NH$_2$ |
| 4 | H-YAibEGTFTSDVSSYLEEIFIQKEFIAWLVRGGPSSGAPPPSK-NH$_2$ |
| 5 | H-HAibEGTFTSDVSSYLEEEAAKEFVNWLLAGGPSSGAPPPSK-NH$_2$ |
| 6 | H-YAibEGTFTSDVSSYLEEEAAKEFVNWLLAGGPSSGAPPPSK-NH$_2$ |
| 7 | H-YAibEGTFTSDVSIYLEKEAAKEFVNWLLAGGPSSGAPPPSK-NH$_2$ |
| 8 | H-YAibEGTFTSDVSIYLEKEAAEEFVNWLLAGGPSSGAPPPSK-NH$_2$ |
| 9 | H-YAibEGTFTSDYSIYLEKEAAKEFVNWLLAGGPSSGAPPPSK-NH$_2$ |
| 10 | H-YAibEGTFTSDYSIYLEKEAAQEFVNWLLAGGPSSGAPPPSK-NH$_2$ |
| 11 | H-YAibEGTFTSDYSIYLEKEAQKEFVNWLLAGGPSSGAPPPSK-NH$_2$ |
| 12 | H-YAibEGTFTSDYSIYLEAibEAAKEFVNWLLAGGPSSGAPPPSK-NH$_2$ |
| 13 | H-YAibEGTFTSDYSIYLEKIAAKEFVNWLLAGGPSSGAPPPSK-NH$_2$ |
| 14 | H-YAibEGTFTSDYSIYLEKIAAQEFVNWLLAGGPSSGAPPPSK-NH$_2$ |
| 15 | H-YAibEGTFTSDYSIYLEKIAQKEFVNWLLAGGPSSGAPPPSK-NH$_2$ |
| 16 | H-YAibEGTFTSDYSIYLEKEAibAKEFVNWLLAGGPSSGAPPPSK-NH$_2$ |
| 17 | H-YAibEGTFTSDYSIYLEKEAAibKEFVNWLLAGGPSSGAPPPSK-NH$_2$ |
| 18 | H-YAibEGTFTSDYSIYLEAibIAAQEFVNWLLAGGPSSGAPPPSK-NH$_2$ |
| 19 | H-YAibEGTFTSDYSIYLDKEAAKEFVNWLLAGGPSSGAPPPSK-NH$_2$ |
| 20 | H-YAibEGTFTSDYSIYLDKIAAQEFVNWLLAGGPSSGAPPPSK-NH$_2$ |
| 21 | H-YAibEGTFTSDYSIYLDKIAAQEFVQWLLAGGPSSGAPPPSK-NH$_2$ |
| 22 | H-YAibEGTFTSDYSIYLDAibIAAQEFVQWLLAGGPSSGAPPPSK-NH$_2$ |
| 23 | H-YAibEGTFTSDYSIYLEKEAAKEFVNWLLAQKPSSGAPPPSK-NH$_2$ |
| 24 | H-YAibEGTFTSDYSIYLEKIAAQEFVNWLLAQKPSSGAPPPSK-NH$_2$ |
| 25 | H-YAibEGTFTSDYSIYLEKEAAKEFVNWLLAGGPSSGAPPPSK(OEG-OEG-yGlu-C18-OH)-NH$_2$ |
| 26 | H-YAibEGTFTSDYSIYLEKEAAKEFVNWLLAGK(OEG-OEG-yGlu-C18-OH)PSSGAPPPS-NH$_2$ |
| 27 | H-YAibEGTFTSDYSIYLEKEAAK(OEG-OEG-yGlu-C18-OH)EFVNWLLAGGPSSGAPPPS-NH$_2$ |
| 28 | H-YAibEGTFTSDYSIYLEKIAAQEFVNWLLAGGPSSGAPPPSK(OEG-OEG-yGlu-C18-OH)-NH$_2$ |
| 29 | H-YAibEGTFTSDYSIYLEKIAAQEFVNWLLAGK(OEG-OEG-yGlu-C18-OH)PSSGAPPPS-NH$_2$ |
| 30 | H-YAibEGTFTSDYSIYLEKIAAK(OEG-OEG-yGlu-C18-OH)EFVNWLLAGGPSSGAPPPS-NH$_2$ |
| 31 | H-YAibEGTFTSDYSIYLEKEAibAKEFVNWLLAGGPSSGAPPPSK(OEG-OEG-yGlu-C18-OH)-NH$_2$ |
| 32 | H-YAibEGTFTSDYSIYLEKEAibAKEFVNWLLAGK(OEG-OEG-yGlu-C18-OH)PSSGAPPPS-NH$_2$ |
| 33 | H-YAibEGTFTSDYSIYLEKEAibAK(OEG-OEG-yGlu-C18-OH)EFVNWLLAGGPSSGAPPPS-NH$_2$ |
| 34 | H-YAibEGTFTSDYSIYLEKIAQQEFIQWLLAGGPSSGAPPPS-NH$_2$ |
| 35 | H-YAibEGTFTSDYSIYLEKIAQQEFIQWLLAQGPSSGAPPPS-NH$_2$ |

-continued

| Compound number | sequence |
|---|---|
| 36 | H-YAibEGTFTSDYSIYLEKIAAQEFIQWLLAGGPSSGAPPPS-NH$_2$ |
| 37 | H-YAibEGTFTSDYSIYLEGIAAQEFIQWLLAGGPSSGAPPPS-NH$_2$ |
| 38 | H-YAibEGTFTSDYSIYLEGIAQQEFIQWLLAGGPSSGAPPPS-NH$_2$ |
| 39 | H-YAibEGTFTSDYSIYLEKIAibQQEFIQWLLAGGPSSGAPPPS-NH$_2$ |
| 40 | H-YAibEGTFTSDYSIYLEKQAAQEFIQWLLAGGPSSGAPPPS-NH$_2$ |
| 41 | H-YAibEGTFTSDYSIYLEKEAAQEFIQWLLAGGPSSGAPPPS-NH2 |
| 42 | H-YAibEGTFTSDYSIYLEGQAAQEFIQWLLAGGPSSGAPPPS-NH$_2$ |
| 43 | H-YAibEGTFTSDYSIYLEEEAAQEFIQWLLAGGPSSGAPPPS-NH$_2$ |
| 44 | H-YAibEGTFTSDYSIYLEGEAAQEFIQWLLAGGPSSGAPPPS-NH$_2$ |
| 45 | H-YAibEGTFTSDYSIYLEEIAAQEFIQWLLAGGPSSGAPPPS-NH$_2$ |
| 46 | H-YAibEGTFTSDYSIYLEEQAAQEFIQWLLAGGPSSGAPPPS-NH$_2$ |
| 47 | H-YAibEGTFTSDYSIYLEKIAAQEFIQWLLAGGPSSGAPPPSK-NH$_2$ |
| 48 | H-YAibEGTFTSDYSIYLEKIAAQEFINWLLAGGPSSGAPPPS-NH$_2$ |
| 49 | H-YAibEGTFTSDYSIYLEKIAAK(OEG-OEG-yGlu-C18-OH)EFINWLLAGG PSSGAPPPS-NH$_2$ |
| 50 | H-YAibEGTFTSDYSIYLEKIAAKEFVNWLLAGK(OEG-OEG-yGlu-C18-OH)PSSGAPPPS-NH$_2$ |
| 51 | H-YAibEGTFTSDYSIYLEKIAAKEFVNWLLAGGPSSGAPPPSK(OEG-OEG-yGlu-C18-OH)-NH$_2$ |
| 52 | H-YAibEGTFTSDYSIYLEKIAAQEFINWLLAGK(OEG-OEG-yGlu-C18-OH)PSSGAPPPS-NH$_2$ |
| 53 | H-YAibEGTFTSDYSIYLEKIAAQEFINWLL AGGPSSGAPPPSK(OEG-OEG-yGlu-C18-OH)-NH$_2$ |
| 54 | H-YAibEGTFTSDYSIYLEKIAQK(OEG-OEG-yGlu-C18-OH)EFVNWLLAG GPSSGAPPPS-NH$_2$ |
| 55 | H-YAibEGTFTSDYSIYLEKIAQKEFVNWLLAGK(OEG-OEG-yGlu-C18-OH)PSSGAPPPS-NH$_2$ |
| 56 | H-YAibEGTFTSDYSIYLEKIAQKEFVNWLLAGGPSSGAPPPSK(OEG-OEG-yGlu-C18-OH)-NH$_2$ |
| 57 | H-YAibEGTFTSDYSIYLEKEAibAK(OEG-OEG-yGlu-C18-OH)EFINWLLA GGPSSGAPPPS-NH$_2$ |
| 58 | H-YAibEGTFTSDYSIYLEKEAibAKEFINWLLAGK(OEG-OEG-yGlu-C18-OH)PSSGAPPPS-NH$_2$ |
| 59 | H-YAibEGTFTSDYSIYLEKEAibAKEFINWLLAGGPSSGAPPPSK(OEG-OEG-yGlu-C18-OH)-NH$_2$ |
| 60 | H-YAibEGTFTSDYSIYLDKIAAK(OEG-OEG-yGlu-C18-OH)EFVNWLLAG GPSSGAPPPS-NH$_2$ |
| 61 | H-YAibEGTFTSDYSIYLDKIAAQEFVNWLLAGK(OEG-OEG-yGlu-C18-OH)PSSGAPPPS-NH$_2$ |
| 62 | H-YAibEGTFTSDYSIYLDKIAAQEFVNWLL AGGPSSGAPPPSK(OEG-OEG-yGlu-C18-OH)-NH$_2$ |
| 63 | H-YAibEGTFTSDYSIYLEKEAAKEFINWLLAGGPSSGAPPPS-NH$_2$ |
| 64 | H-YAibEGTFTSDYSIYLEKEAAKEFVQWLLAGGPSSGAPPPS-NH$_2$ |
| 65 | H-YAibEGTFTSDYSIYLEKEAAKEFIQWLLAGGPSSGAPPPS-NH$_2$ |
| 66 | H-YAibEGTFTSDYSIYLEKEAAKEFVAWLLAGGPSSGAPPPS-NH$_2$ |

-continued

| Compound number | sequence |
|---|---|
| 67 | H-YAibEGTFTSDYSIYLEKEAAKEFIAWLLAGGPSSGAPPPS-NH₂ |
| 68 | H-YAibEGTFTSDVSIYLEKIAAQEFVNWLLAGGPSSGAPPPS-NH₂ |
| 69 | H-YAibEGTFTSDVSIYLDKIAAQEFVNWLLAGGPSSGAPPPS-NH₂ |
| 70 | H-YAibEGTFTSDYSIYLEEIAAQEFVNWLLAGGPSSGAPPPS-NH₂ |
| 71 | H-YAibEGTFTSDYSIYLEEEAAKEFVNWLLAGGPSSGAPPPS-NH₂ |
| 72 | H-YAibEGTFTSDYSIYLEEIAAKEFVNWLLAGGPSSGAPPPS-NH₂ |
| 73 | H-YAibEGTFTSDYSIYLEEEAAQEFVNWLLAGGPSSGAPPPS-NH₂ |
| 74 | H-YAibEGTFTSDYSIYLEKIAAQEFVNWLLAGGPSSGAPPPSK(OEG-OEG-yGlu-C20-OH)-NH₂ |
| 75 | H-YAibEGTFTSDYSIYLEKIAAK(OEG-OEG-yGlu-C20-OH)EFVNWLLAGGPSSGAPPPS-NH₂ |
| 76 | H-YAibEGTFTSDYSIYLEKEAAKEFINWLLAGGPSSGAPPPSK(OEG-OEG-yGlu-C20-OH)-NH₂ |
| 77 | H-YAibEGTFTSDYSIYLEEIAAQEFINWLLAGGPSSGAPPPSK(OEG-OEG-yGlu-C20-OH)-NH₂ |
| 78 | H-YAibEGTFTSDYSIYLEKIAAQEFVQWLLAGGPSSGAPPPS-NH₂ |
| 79 | H-YAibEGTFTSDYSIYLEKIAAQEFVQWLIAGGPSSGAPPPS-NH₂ |
| 80 | H-YAibEGTFTSDYSIYLEKIAAQEFVNWLIAGGPSSGAPPPS-NH₂ |
| 81 | H-YAibEGTFTSDYSIYLEKIAAQEFVQWLLAGGPSSGAPPPSK(OEG-OEG-yGlu-C20-OH)-NH₂ |
| 82 | H-YAibEGTFTSDYSIYLEKIAAQEFVQWLIAGGPSSGAPPPSK(OEG-OEG-yGlu-C20-OH)-NH₂ |
| 83 | H-YAibEGTFTSDYSIYLEKIAAQEFVNWLIAGGPSSGAPPPSK(OEG-OEG-yGlu-C20-OH)-NH₂ |

The present invention also relates to a preferred technical solution, which involves a pharmaceutical composition with the general formula (I), comprising:

1) a therapeutic amount of the GLP-1 analog with the general formula (I) or the pharmaceutically acceptable salt thereof, and 2) a pharmaceutically acceptable excipient or a pharmaceutical carrier.

The present invention also relates to a preferred technical solution, which involves use of the GLP-1 analog with the general formula (I) or the pharmaceutically acceptable salt thereof, and the composition with the general formula (I) in the preparation of a medicament for treatment of non-insulin-dependent diabetes, insulin-dependent diabetes or obesity.

The present invention also relates to a preferred technical solution, which involves the GLP-1 analog with general formula (I) or the pharmaceutically acceptable salt thereof, which is administered simultaneously, separately or successively in combination with one or more reagent(s) selected from the group consisting of metformin, thiazolidinediones, sulfonylurea, dipeptidyl peptidase inhibitors and sodium glucose transporters.

The present invention also relates to a preferred technical solution, which involves the GLP-1 analog with general formula (I) or the pharmaceutically acceptable salt thereof or the composition with general formula (I), which is administered simultaneously, separately or successively in combination with one or more reagent(s) selected from the group consisting of metformin, thiazolidinediones, sulfonylurea, dipeptidyl peptidase inhibitors and sodium glucose transporters.

In another embodiment, the present invention provides the polypeptide compounds and the pharmaceutically acceptable salts thereof as described above.

The polypeptide dual agonist compounds and derivatives thereof provided by the present invention belong to amphoteric compounds, which can be reacted with acidic or basic compounds to form salts by techniques well-known for those skilled in the art. The acid commonly used to form acid addition salt is: hydrochloric acid, hydrobromic acid, hydroiodic acid, sulfuric acid, phosphoric acid, p-toluenesulfonic acid, methanesulfonic acid, oxalic acid, p-bromophenylsulfonic acid, carbonic acid, succinic acid, citric acid, benzoic acid, or acetic acid; salts include sulfate, pyrosulfate, trifluoroacetate, sulfite, bisulfite, phosphate, hydrogen phosphate, dihydrogen phosphate, metaphosphate, pyrophosphate, hydrochloride, bromide, iodide, acetate, propionate, caprylate, acrylate, formate, isobutyrate, caproate, heptanoate, propiolate, oxalate, malonate, succinate, suberate, fumarate, maleate, butyne-1,4-dioate, hexyne-1,6-dioate, benzoate, chlorobenzoate, methylbenzoate, dinitrobenzoate, hydroxybenzoate, methoxybenzoate, phenylacetate, phenylpropionate, phenylbutyrate, citrate, lactate, gamma-hydroxybutyrate, glycolate, tartrate, mesylate, propanesulfonate, naphthalene-1-sulfonate, naphthalene-2-sulfonate, mandelate, etc., preferably trifluoroacetate. Alkaline substances can also form salts with the polypeptide compounds and derivatives thereof provided by the present invention. These alkaline substances include ammonium, hydroxides of alkali metals or alkaline earth metals, as well as carbonates and bicarbonates, typically sodium hydroxide, potassium hydroxide, ammonium hydroxide, sodium carbonate, potassium carbonate, etc.

The pharmaceutical composition comprising the polypeptide dual agonist compound according to the present invention can be used for the treatment of patients in need of such treatment by way of parenteral administration. Parenteral administration can be selected from subcutaneous injection, intramuscular injection or intravenous injection. The polypeptide dual agonist compound of the present invention can also be administered via a transdermal route, such as transdermally administered via a patch, and an ion penetration patch can be selected; or administered via a transmucosal route.

A solid-phase synthesis method is employed for the polypeptide compound and derivatives thereof provided by the present invention. The α-amino group of the amino acid derivatives used in the synthesis process is protected by the Fmoc group (Fluorenyl formyl carbonyl); and based on the difference in functional group, the protective group used for side chain of the amino acid can be selected from the group consisting of: cysteine side chain sulfhydryl, glutamine side chain amino and histidine side chain imidazolyl are protected by Trt (triphenylmethyl); and arginine side chain guanidyl is protected by Pbf (2,2,4,6,7-pentamethyldihydrobenzofuran-5-sulfonyl); tryptophan side chain indolyl, lysine side chain amino are protected by Boc (tert-butoxycarbonyl); threonine side chain hydroxyl, tyrosine side chain phenol group and serine side chain hydroxyl are protected by t-Bu (tert-butyl). During the process of synthesis, the carboxyl group of the C-terminal amino acid residue of the polypeptide is firstly condensed onto the polymer insoluble Rink-amide ChemMatrix resin in the form of an amide bond, then the Fmoc protective group is removed from the α-amino group by using N,N-dimethylformamide (DMF) solution comprising 20% piperidine, and then the solid phase carrier is condensed with the next amino acid derivative in the sequence in excess to form an amide bond, so as to extend the peptide chain. The procedures of condensation→washing→deprotection→washing→the next round of amino acid condensation are repeated, until the desirable length of the polypeptide chain to be synthesized is achieved, and finally the polypeptide is cleaved from the solid phase carrier by reacting a mixture of trifluoroacetic acid:water:triisopropylsilane (90:5:5, v:v:v) with the resin, and then precipitated with frozen isopropyl ether, resulting in a solid crude product of the polypeptide derivative. The solid crude product of the polypeptide is dissolved in a mixture of acetonitrile/water comprising 0.1% trifluoroacetic acid, purified and separated by a C-18 reversed phase preparative chromatography column, the pure product of the polypeptide and derivatives thereof is obtained.

DETAILED DESCRIPTION OF THE INVENTION

Unless stated to the contrary, the terms used in the specification and claims have the following meanings.

The amino acid sequence of the present invention comprises standard one-letter or three-letter codes for twenty amino acids. Unless explicitly stated otherwise, the preferred configuration of all amino acid residues in the present invention is L-configuration. In addition, Aib refers to α-aminoisobutyric acid and D-Ala refers to D-alanine.

The term agonist is defined as a substance that activates the type of receptor in discussion:

As used in the context of the present invention, the term GLP-1/GIP dual agonist refers to a substance or ligand that can activate both GLP-1 receptor and GIP receptor. In the present invention, the term treatment includes inhibiting, slowing down, stopping or reversing the existing symptoms or the progress or severity of the disease.

"Natural amino acids" refer to 20 types of conventional amino acids (i.e. Alanine (A), Cysteine (C), Aspartic acid (D), Glutamic acid (E), Phenylalanine (F), Glycine (G), Histidine (H), Isoleucine (I), Lysine (K), Leucine (L), Methionine (M), Asparagine (N), Proline (P), Glutamine (Q), Arginine (R), Serine (S), Threonine (T), Valine (V), Tryptophan (W) and Tyrosine (Y).

"Unnatural amino acid" refers to an amino acid that is not naturally encoded or found in the genetic code of any organism. They can be, for example, purely synthetic compounds. Examples of unnatural amino acids include, but are not limited to, hydroxyproline, γ-carboxyglutamic acid, O-phosphoserine, azetidine carboxylic acid, 2-aminoadipate, 3-aminoadipate, β-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tert-butylglycine, 2,4-diaminoisobutyric acid (Dap), desmosine, 2,2'-diaminopimelic acid, 2,3-diaminopropionic acid (Dab), N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine (Om), D-ornithine, D-arginine, p-aminophenylalanine acid, pentylglycine, pipecolic acid and thioproline. In addition, natural or unnatural amino acids which are chemically modified on C-terminal carboxyl group, N-terminal amino group and/or side chain functional group are also included.

The term "alkyl" refers to a saturated aliphatic alkyl group, which is a linear or branched chain group comprising 1 to 20 carbon atoms, preferably an alkyl group comprising 1 to 8 carbon atoms, more preferably an alkyl group comprising 1 to 6 carbon atoms, most preferably an alkyl group of 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-Dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferred are lower alkyl groups comprising 1 to 6 carbon atoms, non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. Alkyl groups may be substituted or unsubstituted. When substituted, substituents can be substituted at any available attachment point. The substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkyloxy, heterocycloalkoxy, cycloalkylthio, heterocycloalkylthio, oxo, carboxy, or carboxylate, preferably in the present invention is methyl, ethyl, isopropyl, tert-butyl, haloalkyl, deuterated alkyl, alkoxy-substituted alkyl and hydroxy-substituted alkyl.

"X is selected from A, B, or C", "X is selected from the group consisting of A, B and C", "X is A, B or C", "X is A, B and C" and other terms all express the same meaning, which means that X can be any one or more of A, B, and C.

The "modification" of amino acids described in this patent refers to the substitution, addition or deletion of amino acids, including substitution or addition of any of the 20 natural amino acids.

The term "natural GLP-1" refers to a peptide comprising the human GLP-1 (7-36 or 7-37) sequence, and the term "natural GIP" refers to a peptide comprising the human GIP (1-42) sequence.

The terms "GLP-1" or "GIP", if not explained further, refer to natural GLP-1 or natural GIP, respectively.

The "substitution" of an amino acid described in this patent refers to the substitution of an amino acid residue by a different amino acid residue.

The term "polyethylene glycol" or "PEG" refers to the mixture of the condensation polymer of ethylene oxide and water, which exists in linear or branched form and is represented by the general formula of $H(OCH_2CH_2)_nOH$, wherein n is no less than 9. Unless otherwise specified, this term includes polyethylene glycol polymers with an average total molecular weight between 5,000 and 40,000 Daltons.

The term "polyethylene glycol" or "PEG" is used with a numerical suffix to indicate its approximate average molecular weight. For example, PEG-5000 refers to polyethylene glycol having an average molecular weight of about 5000 Daltons.

The term "PEGylation" or similar terms refer to the modification of compound in natural state by linking a PEG chain to a peptide.

The term "PEGylated peptide" refers to a peptide in which a PEG chain is covalently bound to the peptide.

The term "fatty acid" refers to a carboxylic acid with a long fatty acid tail (chain), which can be saturated or unsaturated; in the present invention, the fatty acid refers to a carboxylic acid with C4-C30 linear or branched aliphatic groups.

The general definition of peptides described in this patent includes peptides with modified amino and carboxyl terminus. For example, amino acid sequence designated as a natural amino acid also includes an amino acid chain comprising a terminal carboxylic acid substituted with an amide group.

The hydrogen atoms described in the present invention can be replaced by its isotope deuterium, and any hydrogen atom in the exemplary compounds of the present invention can also be replaced by a deuterium atom.

"Optional" or "optionally" means that the event or circumstance that follows the term may, but does not necessarily, occur; and the description includes the instances in which the event or circumstance does or does not occur. For example, "heterocyclic group optionally substituted by an alkyl group" means that the alkyl group may be (but not necessarily) present, and the description includes the instances where the heterocyclic group is substituted by the alkyl group and the instances where the heterocyclic group is not substituted by the alkyl group.

"Substituted" refers to one or more hydrogen atoms in a group, preferably up to 5, more preferably 1 to 3 hydrogen atoms independently substituted by a corresponding number of substituents. It is obvious that the substituents are only located at possible chemical positions, and those skilled in the art can determine (by experiment or theory) possible or impossible substitutions without undue effort. For example, the binding of an amino group or a hydroxyl group having free hydrogen to a carbon atom having an unsaturated bond (e.g., olefinic) may be unstable.

"Pharmaceutical composition" refers to a mixture comprising one or more compounds described herein or a physiologically/pharmaceutically acceptable salt or produg thereof and other chemical components, such as physiologically/pharmaceutically acceptable carriers and excipients. The pharmaceutical composition aims at promoting the administration to an organism, facilitating the absorption of the active ingredient and thereby exerting a biological effect.

"Pharmaceutically acceptable salt" refers to the salt of the compound of the present invention, which is safe and effective when applied to mammals in vivo, and has expected biological activity.

DETAILED DESCRIPTION OF THE PARTICULAR EMBODIMENTS

In order to describe the present invention in more detail, this specification provides the following specific embodiments, but the technical solution of the present invention is not limited to the embodiments.

1. Experimental Reagents

| Serial number | Reagent | Source |
|---|---|---|
| 1 | Rink-amide ChemMatrix resin | Biotage |
| 2 | DEPBT | GL Biochem |
| 3 | Fmoc-Aib-OH | GL Biochem |
| 4 | Fmoc-L-Lys(Mtt)-OH | GL Biochem |
| 5 | N,N-Dimethylformamide | Sinopharm reagent |
| 6 | Dichloromethane | Sinopharm reagent |
| 7 | Trifluoroacetic acid | Sinopharm reagent |
| 8 | Triisopropylsilane | Sigma-Aldrich |
| 9 | Hexafluoroisopropanol | Sigma-Aldrich |
| 10 | Acetonitrile | Merck-Millipore |
| 11 | Diisopropylethylamine | Sigma-Aldrich |
| 12 | Piperidine | Merck-Millipore |
| 13 | Anhydrous isopropyl ether | INEOS Solvents |
| 14 | Boc-L-Tyr(tBu)—OH | GL Biochem |
| 15 | Fmoc-H-PEG$_2$-COOH | GL Biochem |
| 16 | Fmoc-L-Glu-OtBu | GL Biochem |
| 17 | HOOC—$(CH_2)_{16}$—COOtBu | GL Biochem |

2. Experimental Instrument

| Serial number | Instrument | Source |
|---|---|---|
| 1 | H-CLASS Analytical Ultra Performance Liquid Chromatography | WATERS |
| 2 | Xevo Lquid Chromatography/ Mass Spectrometry | WATERS |
| 3 | Labconco Multifunctional Freeze Dryer | Thermo-Fisher Scientific |
| 4 | Prep150 Preparative High Performance Liquid Chromatography | WATERS |
| 5 | Multi-channel High-Speed Centrifuge | Sigma |

3. Specific Experimental Scheme 3.1 Chemical Synthesis of Polypeptide Backbone Compound No. 1

3.1.1 Coupling of Fmoc-L-Lys(Boc)-OH to Rink-Amide ChemMatrix Resin

Rink-amide ChemMatrix resin (Biotage, 0.1 mmol) was weighed and placed into a disposable polypropylene polypeptide synthesis solid-phase reaction tube; DMF (10 ml) was added to swell the resin under nitrogen bubbling for 10 minutes; DMF was removed under vacuum, and DMF (10 ml) was added to wash the resin; the washing was repeated for twice; Fmoc-L-Lys(Boc)-OH (1 mmol), 3-(diethoxy-phosphyloxy)-1,2,3-benzotriazin-4-one (DEPBT) (1 mmol) and diisopropylethylamine (DIEA, 2 mmol) were weighed and dissolved by adding DMF (10 ml), and then loaded onto the swollen Rink-amide ChemMatrix resin. The reaction was performed with shaking at room temperature for 2 hours. After the reaction was completed, the resin was washed alternately with DMF and dichloromethane (DCM) for twice, and finally washed with DMF for three times.

3.1.2 Removal of Fmoc Protective Group with Fmoc-L-Lys(Boc)-Rink-Amide Resin Piperidine/DMF (20%, 10 ml) was added into the solid-phase reaction tube comprising Fmoc-L-Lys(Boc)-Rink amide resin. The reaction was performed with shaking at room temperature for 10 minutes; then piperidine/DMF (20%, 10 ml) was added and shaken at room temperature for 10 minutes, and then removed. After the reaction was completed, the resin was washed with DMF (10 ml) for 4 times.

3.1.3 Coupling of Peptide Chain Sequences

According to the peptide chain sequence of compound No. 1, from the amino terminus to the carboxy terminus (H-His-Aib-Glu-Gly-Thr-Phe-Thr-Ser-Asp-Val-Ser-Ser-Tyr-Leu-Glu-Glu-Glu-Ala-Al a-Lys-Glu-Phe-Ile-Ala-Trp-Leu-Val-Arg-Gly-Gly-Pro-Ser-Ser-Gly-Ala-Pro-Pro-Pro-S er-Lys-NH$_2$), the amount of amino acid derivatives and condensation reagents and their condensation methods were the same as those used for coupling Fmoc-L-Lys(Boc)-OH onto Rink-amide ChemMatrix resin. The amino acid residues used in the synthesis process were: Fmoc-L-His(Trt)-OH, Fmoc-Aib-OH, Fmoc-L-Glu(OtBu)-OH, Fmoc-Gly- OH, Fmoc-L-Thr(tBu)-OH, Fmoc-L-Phe-OH, Fmoc-L-Ser (tBu)-OH, Fmoc-L-Asp(OtBu)-OH, Fmoc-L-Val-OH, Fmoc-Tyr(tBu)-OH, Fmoc-L-Ala-OH, Fmoc-L-Lys(Boc)-OH, Fmoc-L-Ile-OH, Fmoc-L-Trp(Boc)-OH, Fmoc-L-Leu-OH, Fmoc-L-Arg(Pbf)-OH and Fmoc-L-Pro-OH. The condensation of amino acid derivatives and Fmoc deprotection were repeated, finally resulting in the resin peptide comprising the polypeptide sequence of Compound No. 1.

3.1.4 Cleavage of Resin Peptides

The resin peptide resulted from step 3 was washed successively with DMF and DCM for 3 times and then dried under vacuum. Then 10 ml of freshly prepared lysate (trifluoroacetic acid:triisopropylsilane:water=90:5:5, v:v:v) was added. The reaction was performed with shaking at room temperature for 2 hours. Filtration was carried out after the reaction was completed, and the resin was washed for twice with trifluoroacetic acid. The filtrate was pooled, and then a large amount of frozen anhydrous isopropyl ether was added to precipitate a solid. After centrifugation, the supernatant was removed and the crude polypeptide product of Compound No. 1 was obtained.

3.1.5 Purification of the Crude Peptides by Reversed Phase Liquid Chromatography The crude peptide was dissolved in a mixed solvent comprising 0.1% trifluoroacetic acid and 20% acetonitrile/water, filtered through a 0.22 um membrane, and subjected to isolation by using WATERS Prep150 LC reversed-phase high performance liquid chromatography system. Buffer A (0.10% trifluoroacetic acid, 10% acetonitrile in water) and B (0.1% trifluoroacetic acid, 90% acetonitrile in water). Among them, the chromatographic column was X-SELECT OBD C-18 (WATERS) reversed-phase chromatographic column. During the purification process, the detection wavelength of the chromatography was set to 220 nm, and the flow rate was 20 mL/min. The relevant fractions of the product were collected and lyophilized to obtain the pure polypeptide product of Compound No. 1, with a yield of 20%. The purity and identity of the pure polypeptide product were determined by analytical high performance liquid chromatography and liquid chromatography/mass spectrometry. The purity was 95.38%, and the molecular weight of the compound was 4218.4.

3.2 Chemical Synthesis of Compound Nos 2-24, 34-48, 63-73 and 78-80

The polypeptide compounds of the present invention under the compound Nos 2-24, 34-48, 63-73 and 78-80 were synthesized according to the experimental scheme for compound 1, and the purity and molecular weight of the compounds were determined by analytical ultra-high performance liquid chromatography and liquid chromatography/mass spectrometry. Specifically, as shown in Table 1 below:

TABLE 1

| Compound number | Purity | Molecular weight |
|---|---|---|
| 2 | 95.06% | 4244.8 |
| 3 | 97.98% | 4369.6 |
| 4 | 96.34% | 4353.2 |
| 5 | 96.05% | 4178.0 |
| 6 | 95.29% | 4203.3 |
| 7 | 95.15% | 4227.6 |

TABLE 1-continued

| Compound number | Purity | Molecular weight |
|---|---|---|
| 8 | 95.05% | 4230.3 |
| 9 | 95.95% | 4293.2 |
| 10 | 95.56% | 4292.1 |
| 11 | 96.33% | 4350.0 |
| 12 | 95.60% | 4249.5 |
| 13 | 96.86% | 4277.4 |
| 14 | 95.58% | 4277.4 |
| 15 | 97.64% | 4333.8 |
| 16 | 95.07% | 4307.4 |
| 17 | 97.76% | 4307.4 |
| 18 | 96.53% | 4233.9 |
| 19 | 95.11% | 4278.6 |
| 20 | 96.79% | 4262.7 |
| 21 | 98.73% | 4276.8 |
| 22 | 96.87% | 4233.6 |
| 23 | 95.69% | 4434.4 |
| 24 | 96.72% | 4419.3 |
| 34 | 95.65% | 4233.6 |
| 35 | 96.56% | 4304.7 |
| 36 | 96.74% | 4176.6 |
| 37 | 96.65% | 4105.5 |
| 38 | 95.24% | 4162.5 |
| 39 | 95.14% | 4247.7 |
| 40 | 95.75% | 4191.6 |
| 41 | 95.56% | 4192.5 |
| 42 | 95.74% | 4120.4 |
| 43 | 96.84% | 4193.5 |
| 44 | 95.24% | 4121.4 |
| 45 | 96.54% | 4177.5 |
| 46 | 95.77% | 4192.5 |
| 47 | 97.55% | 4304.8 |
| 48 | 95.32% | 4162.6 |
| 63 | 97.14% | 4178.6 |
| 64 | 96.32% | 4178.6 |
| 65 | 95.47% | 4193.3 |
| 66 | 96.56% | 4122.5 |
| 67 | 98.87% | 4136.4 |
| 68 | 96.54% | 4085.2 |
| 69 | 95.24% | 4071.1 |
| 70 | 96.14% | 4150.5 |
| 71 | 96.78% | 4166.6 |
| 72 | 95.69% | 4150.4 |
| 73 | 96.32% | 4165.3 |
| 78 | 95.18% | 4162.6 |
| 79 | 96.22% | 4162.6 |
| 80 | 97.21% | 4148.5 |

3.3 Chemical Synthesis of Compound No. 25 Coupled with Fatty Acid

3.3.1 Coupling of Fmoc-L-Lys(Mtt)-OH onto Rink-Amide ChemMatrix Resin

Rink-amide ChemMatrix resin (Biotage, 0.1 mmol) was weighed and placed into a disposable polypropylene polypeptide synthesis solid-phase reaction tube, DMF (10 ml) was added to swell the resin under nitrogen bubbling for 10 minutes, DMF was removed under vacuum, and DMF (10 ml) was added to wash the resin, the washing was repeated for twice; Fmoc-L-Lys(Mtt)-OH (1 mmol), 3-(diethoxyphosphyloxy)-1,2,3-benzotriazin-4-one (DEPBT) (1 mmol) and diisopropylethylamine (DIEA, 2 mmol) were weighed and dissolved by adding DMF (10 ml), and then loaded onto the swollen Rink-amide ChemMatrix resin. The reaction was performed with shaking at room temperature for 2 hours. After the reaction was completed, the resin was washed alternately with DMF and dichloromethane (DCM) for twice, and finally washed with DMF for three times.

3.3.2 Fmoc Deprotection and Peptide Chain Extension

The Fmoc deprotection from Fmoc-L-Lys(Mtt)-Rink amide ChemMatrix resin and the subsequent peptide chain extension were performed according to the same synthetic method as in Example 1, resulting in a resin peptide comprising Compound No. 25, wherein Boc-L-Tyr(t-Bu)-OH was used as the N-terminal amino acid residue.

3.3.3 Mtt Deprotection and Lysine Side Chain Modification of Resin Peptide

After the above peptide-resin extension was completed, a mixture of hexafluoroisopropanol/dichloromethane (30%, 10 ml) was added, shaken and reacted at room temperature for 45 minutes and then removed. Then a mixture of hexafluoroisopropanol/dichloromethane (30%, 10 ml) was added again, shaken and reacted at room temperature for 45 minutes and then removed. After the reaction was completed, the resin was washed with DMF for 6 times. The additional coupling/deprotection cycle by using Fmoc/tBu solid phase synthesis strategy to extend the side chain of lysine involves Fmoc-NH-PEG2-COOH, Fmoc-L-Glu-OtBu and HOOC—$(CH_2)_{16}$—COOt-Bu. In all couplings, the reaction was carried out at room temperature, and 1 mmol of amino acid construct, 1 mmol of DEPBT and 2 mmol of DIEA were reacted in DMF for 4 hours.

3.3.4 Cleavage and Purification of the Product

The resin peptide resulted from the above steps was washed successively with DMF and DCM for twice and then dried under vacuum. Then the freshly prepared lysate was added (trifluoroacetic acid:triisopropylsilane:water=90:5:5, v:v:v). The reaction was performed with shaking at room temperature for 2 hours. Filtration was carried out after the reaction was completed, and the resin was washed for twice with trifluoroacetic acid. The filtrate was pooled, and then a large amount of frozen anhydrous isopropyl ether was added to precipitate a solid. After centrifugation, the supernatant was removed and the crude polypeptide product of Compound No. 25 was obtained.

3.3.5 Purification of Compound 25 with Reversed-Phase Liquid Chromatography The crude peptide was dissolved in a mixed solvent comprising 0.1% trifluoroacetic acid and 20% acetonitrile/water, filtered through a 0.22 μm membrane, and subjected to isolation by using WATERS Prep150 LC reversed-phase high performance liquid chromatography system. Buffer A (0.10% trifluoroacetic acid, 10% acetonitrile in water) and B (0.1% trifluoroacetic acid, 90% acetonitrile in water). Among them, the chromatographic column was X-SELECT OBD C-18 reversed-phase chromatographic column. During the purification process, the detection wavelength of the chromatography was set to 220 nm, and the flow rate was 20 mL/min. The relevant fractions of the product were collected and lyophilized to obtain the pure polypeptide product of Compound No. 25, with a yield of 18%. The purity and molecular weight of the pure polypeptide product were determined by analytical high performance liquid chromatography and liquid chromatography/mass spectrometry. The purity was 96.23%, and the molecular weight of the compound was 5008.6.

3.4 Chemical Synthesis of Compound Nos 26-33 and 49-62

The polypeptide compounds of the present invention (compound Nos 26-33) were synthesized according to the experimental scheme for compound 25, and the purity and molecular weight of the compounds were determined by analytical high performance liquid chromatography and liquid chromatography/mass spectrometry. Specifically, as shown in Table 2 below:

TABLE 2

| Compound number | Purity | Molecular weight |
| --- | --- | --- |
| 26 | 96.01% | 4951.6 |
| 27 | 95.04% | 4880.5 |
| 28 | 96.56% | 4992.6 |
| 29 | 96.36% | 4935.5 |
| 30 | 95.64% | 4864.4 |
| 31 | 95.45% | 5022.6 |
| 32 | 95.36% | 4965.6 |
| 33 | 95.41% | 4894.4 |
| 49 | 95.92% | 4864.4 |
| 50 | 96.31% | 4936.6 |
| 51 | 95.14% | 4992.6 |
| 52 | 96.58% | 4992.6 |
| 53 | 95.74% | 4921.5 |
| 54 | 97.63% | 4992.6 |
| 55 | 95.54% | 5049.7 |
| 56 | 97.24% | 4894.4 |
| 57 | 96.64% | 4965.6 |
| 58 | 95.27% | 5022.6 |
| 59 | 96.64% | 4850.4 |
| 60 | 95.65% | 4921.5 |
| 61 | 96.67% | 4978.6 |
| 62 | 95.32% | 4992.6 |

3.5 Chemical Synthesis of Compound No. 74

3.5.1 Coupling of Fmoc-L-Lys(Mtt)-OH onto Rink-Amide ChemMatrix Resin

Rink-amide ChemMatrix resin (Biotage, 0.1 mmol) was weighed and placed into a disposable polypropylene polypeptide synthesis solid-phase reaction tube, DMF (10 ml) was added to swell the resin under nitrogen bubbling for 10 minutes, DMF was removed under vacuum, and DMF (10 ml) was added to wash the resin, the washing was repeated for twice; Fmoc-L-Lys(Mtt)-OH (1 mmol), 3-(diethoxy-phosphyloxy)-1,2,3-benzotriazin-4-one (DEPBT) (1 mmol) and diisopropylethylamine (DIEA, 2 mmol) were weighed and dissolved by adding DMF (10 ml), and then loaded onto the swollen Rink-amide ChemMatrix resin. The reaction was performed with shaking at room temperature for 2 hours. After the reaction was completed, the resin was washed alternately with DMF and dichloromethane (DCM) for twice, and finally washed with DMF for three times.

3.5.2 Fmoc Deprotection and Peptide Chain Extension

The Fmoc deprotection from Fmoc-L-Lys(Mtt)-Rink amide ChemMatrix resin and the subsequent peptide chain extension were performed according to the same synthetic method as in Example 1, resulting in a resin peptide comprising Compound No. 74, wherein Boc-L-Tyr(t-Bu)-OH was used as the N-terminal amino acid residue.

3.5.3 Mtt Deprotection and Lysine Side Chain Modification of Resin Peptide

After the above peptide-resin extension was completed, a mixture of hexafluoroisopropanol/dichloromethane (30%, 10 ml) was added, shaken and reacted at room temperature for 45 minutes and then removed. Then a mixture of hexafluoroisopropanol/dichloromethane (30%, 10 ml) was added again, shaken and reacted at room temperature for 45 minutes and then removed. After the reaction was completed, the resin was washed with DMF for 6 times. The additional coupling/deprotection cycle by using Fmoc/tBu solid phase synthesis strategy to extend the side chain of lysine involves Fmoc-NH-PEG2-COOH, Fmoc-L-Glu-OtBu and HOOC—$(CH_2)_{18}$—COOt-Bu. In all coupling reactions, the reaction was carried out at room temperature, and 1 mmol of amino acid construct, 1 mmol of DEPBT and 2 mmol of DIEA were reacted in DMF for 4 hours.

3.5.4 Cleavage and Purification of the Product

The resin peptide resulted from the above steps was washed successively with DMF and DCM for twice and then dried under vacuum. Then the freshly prepared lysate was added (trifluoroacetic acid:triisopropylsilane:water=90:5:5, v:v:v). The reaction was performed with shaking at room temperature for 2 hours. Filtration was carried out after the reaction was completed, and the resin was washed for twice with trifluoroacetic acid. The filtrate was pooled, and then a large amount of frozen anhydrous isopropyl ether was added to precipitate a solid. After centrifugation, the supernatant was removed and the crude polypeptide product of Compound No. 74 was obtained.

3.5.5 Purification of Compound 74 with Reversed-Phase Liquid Chromatography The crude peptide was dissolved in a mixed solvent comprising 0.1% trifluoroacetic acid and 20% acetonitrile/water, filtered through a 0.22 μm membrane, and subjected to isolation by using WATERS Prep150 LC reversed-phase high performance liquid chromatography system. Buffer A (0.1% trifluoroacetic acid, 10% acetonitrile in water) and B (0.1% trifluoroacetic acid, 90% acetonitrile in water). Among them, the chromatographic column was X-SELECT OBD C-18 reversed-phase chromatographic column. During the purification process, the detection wavelength of the chromatography was set to 220 nm, and the flow rate was 20 mL/min. The relevant fractions of the product were collected and lyophilized to obtain the pure polypeptide product of Compound No. 74, with a yield of 18%. The purity and molecular weight of the pure polypeptide product were determined by analytical high performance liquid chromatography and liquid chromatography/mass spectrometry. The purity was 95.14%, and the molecular weight of the compound was 5020.6.

3.6 Chemical Synthesis of Compound Nos 75-77 and 81-83

The polypeptide compounds of the present invention (compound Nos 75-77 and 81-83) were synthesized according to the experimental scheme for compound 74, and the purity and molecular weight of the compounds were determined by analytical high performance liquid chromatography and liquid chromatography/mass spectrometry. Specifically, as shown in Table 3 below:

TABLE 3

| Compound number | Purity | Molecular weight |
|---|---|---|
| 75 | 95.91% | 4892.5 |
| 76 | 96.25% | 5047.6 |
| 77 | 95.36% | 5035.6 |
| 81 | 96.31% | 5034.7 |
| 82 | 97.22% | 5034.7 |
| 83 | 95.61% | 5020.6 |

Biological Test and Evaluation

The following test examples are provided to further describe the present invention, but are not intended to limit the scope of the invention.

1. Experimental Reagents

| Serial number | Reagent | Source |
|---|---|---|
| 1 | DMEM/F12 | Gibco 11330032 |
| 2 | Casein | Sigma C3400-500G |
| 3 | 3-Isobutyl-1-methylxanthine | Sigma I7018-250MG |
| 4 | cAMP-Gs Dynamic kit-20,000 tests | Cisbio 62AM4PEC |
| 5 | Corning ® 384 well microplate, low volume | Sigma CLS4514-50EA |
| 6 | 96V-bottom plate (PS) | Axygen WIPP02280 |
| 7 | Countess ® Cell Counting Chamber Slides | Invitrogen C10228 |
| 8 | puromycin | ThermoFisher A1113803 |
| 9 | Hygromycin B | Sigma A1720 |
| 10 | PBS | Gibco 10010023 |
| 11 | 0.25% Trypsin-EDTA(1X), Phenol Red | ThermoFisher 25200-114 |
| 12 | Gibco ™ Fetal Bovine Serum, Qualified, Australia Origin | ThermoFisher 10099-141 |
| 13 | glucose | Sigma G8270-100G |

2. Experimental Instrument

| Serial number | Instrument | Source |
|---|---|---|
| 1 | $CO_2$ incubator | Thermo 311 |
| 2 | Biosafety cabinet | Shanghai BOXUN BSC-1300IIA2 |
| 3 | Refrigerated centrifuge | Eppendorf 5702R |
| 4 | Haier double-door household refrigerator | Haier BCD-268TN |
| 5 | Cell counter | Life Technologies CountessII |
| 6 | Medicine storage box | Haier hyc-940 |
| 7 | Minus 20 degrees Celsius refrigerator | Haier DW-25L262 |
| 8 | Refrigerated centrifuge 5810R | Eppendorf 5810R |
| 9 | Automatic dispenser (Multidrop) | Thermo 5840300 |
| 10 | Microplate reader | BioTek H1MFD |
| 11 | $CO_2$ bacteria incubator | Shanghai BOXUN BC-J80S |
| 12 | ACCU-CHEK Active | Roche |

3. Test Example 3.1. Evaluation of the Agonistic Activity of the Test Compounds for the Glucagon-Like Peptide-1 Receptor (GLP-1R)

3.1.1 The Purpose of the Experiment

The purpose of this test example is to measure the agonistic activity of the numbered compounds for the glucagon-like peptide-1 receptor (GLP-1R).

3.1.2 Experimental Method

The frozen CHO-K1/GLP-1R/CRE-luc stably transfected cell line was taken out from the liquid nitrogen tank, quickly thawed in a 37° C. water bath, and re-suspended in DMEM/F12 medium (Gibco Cat #11330032). After centrifugation, the cells were washed once, resuspended in the experimental buffer (DMEM/F12 medium comprising 0.1% casein (Sigma Cat #C3400)), and the cell density was adjusted with the experimental buffer. The cells were plated at a density of 2500 cells/5 µL/well in a 384-well plate (Sigma Cat #CLS4514), and then 2.5 µL of IBMX working solution (Sigma Cat #17018) prepared with buffer solution (the final concentration of IBMX was 0.5 mM) and 2.5 µL of the gradient diluted polypeptide sample were added into each well, centrifuged at 1000 rpm for 1 min, shaken for 30 seconds to mix well, and incubated at room temperature for 30 minutes. Cisbio cAMP-Gs Dynamic kit (Cisbio Cat #62AM4PEC) was used for detection. cAMP-d2 and Anti-cAMP-Eu$^{3+}$-Cryptate were diluted with 20-fold cAMP Lysis & Detection Buffer respectively, and mixed well. 5 µL of the diluted cAMP-d2 solution was added into each well, and then 5 µL of the diluted Anti-cAMP-Eu$^{3+}$-Cryptate solution was added into each well, shaken for 30 seconds to mix well, and incubated at room temperature for 1 hour in the dark.

3.1.3 Method for Processing Experimental Data

HTRF signals were read with Biotek Synergy H1 microplate reader, with the excitation wavelength of 320 nm, and emission wavelength of 620 nm and 665 nm. The signal ratio (665 nm/620 nm*10,000) was calculated, and the signal ratio was nonlinear fitted to the sample concentration with four-parameter equation in GraphPad Prism 6, resulting in the $EC_{50}$ values. The particular data are shown in Table 4 below.

3.2. Evaluation of the Agonistic Activity of the Test Compounds for the Glucose-Dependent Insulinotropic Peptide Receptor (GIPR)

3.2.1 The Purpose of the Experiment

The agonistic activity of the test compounds for the glucose-dependent insulinotropic peptide receptor (GIPR).

3.2.2 Experimental Method

Wild-type CHO-K1 cells were collected, and the cell suspension was adjusted to an appropriate density, plated in a 6-well plate at 2 mL per well, and placed in a 37° C., 5% $CO_2$ incubator for adhesion overnight. The mixture for transfection (hGIPR plasmid, Fugene HD (Promega Cat #E2311), OptiMEM (Gibco Cat #31985070)) was mixed well, placed at room temperature for 15 minutes, and was added at 100 µL to the corresponding cell well. After transfection of CHO-K1 cells for 24 h, hGIPR was over-expressed on the cell surface. The cells in 6-well plate were collected after the transient transfection, and were washed once with the experimental buffer (DMEM/F12 medium (Gibco Cat #11330032) comprising 0.1% casein (Sigma Cat #C3400)), and the cell density was adjusted with the experimental buffer. The cells were plated at a density of 5000 cells/5 µL/well in a 384-well plate (Sigma Cat #CLS4514), and then 2.5 µL of IBMX working solution (Sigma Cat #17018) prepared with buffer solution (the final concentration of IBMX was 0.5 mM) and 2.5 µL of the gradient diluted polypeptide sample were added into each well, centrifuged at 1000 rpm for 1 min, shaken for 30 seconds to mix well, and incubated at room temperature for 30 minutes. Cisbio cAMP-Gs Dynamic kit (Cisbio Cat #62 AM4PEC) was used for detection. cAMP-d2 and Anti-cAMP-Eu3+-Cryptate were diluted with 20-fold cAMP Lysis & Detection Buffer respectively, and mixed well. 5 µL of the diluted cAMP-d2 solution was added into each well, and then 5 µL of the diluted Anti-cAMP-Eu3+-Cryptate solution was added into each well, shaken for 30 seconds to mix well, and incubated at room temperature for 1 hour in the dark.

3.2.3 Method for Processing Experimental Data

HTRF signal was read with Biotek Synergy H1 microplate reader, with the excitation wavelength of 320 nm, and emission wavelength of 620 nm and 665 nm. The signal ratio (665 nm/620 nm*10,000) was calculated, and the signal ratio was nonlinear fitted to the sample concentration with four-parameter equation in GraphPad Prism 6, resulting in the $EC_{50}$ values. The particular data are shown in Table 4 below.

Agonistic activity of the polypeptide backbone compounds for human GLP-1R and human GIPR receptors.

TABLE 4

| Compound | Activity for human GLP-1R ($EC_{50}$ nM) | Activity for human GIPR ($EC_{50}$ nM) |
|---|---|---|
| Natural GLP-1 | 0.007 | N/A |
| Natural GIP | N/A | 0.003 |
| Semaglutide | 0.025 | >10 |
| 1 | 0.005 | >10 |
| 2 | 0.017 | 3.5 |
| 3 | 0.578 | 0.91 |
| 4 | 0.43 | >10 |
| 5 | 0.004 | >10 |
| 6 | 0.128 | 2.1 |
| 7 | 0.016 | 0.16 |
| 8 | 0.070 | 0.12 |
| 9 | 0.011 | 0.018 |
| 10 | 0.097 | 0.006 |
| 11 | 0.080 | 0.014 |
| 12 | 0.013 | 0.081 |
| 13 | 0.013 | 0.017 |
| 14 | 0.008 | 0.006 |
| 15 | 0.015 | 0.009 |
| 16 | 0.007 | 0.018 |
| 17 | 0.010 | 0.057 |
| 18 | 0.022 | 0.012 |
| 19 | 0.024 | 0.020 |
| 20 | 0.027 | 0.008 |
| 21 | 0.043 | 0.015 |
| 22 | 0.051 | 0.018 |
| 23 | 0.059 | 0.020 |
| 24 | 0.083 | 0.008 |
| 63 | 0.010 | 0.020 |
| 64 | 0.020 | 0.033 |
| 65 | 0.013 | 0.027 |

TABLE 4-continued

| Compound | Activity for human GLP-1R ($EC_{50}$ nM) | Activity for human GIPR ($EC_{50}$ nM) |
|---|---|---|
| 66 | 0.026 | 0.054 |
| 67 | 0.025 | 0.017 |
| 68 | 0.025 | 0.047 |
| 69 | 0.052 | 0.120 |
| 70 | 0.017 | 0.017 |
| 71 | 0.017 | 0.042 |
| 72 | 0.017 | 0.030 |
| 73 | 0.069 | 0.021 |
| 78 | 0.008 | 0.012 |
| 79 | 0.012 | 0.015 |
| 80 | 0.008 | 0.008 |

Experimental Conclusion

By designing and studying the polypeptide skeleton/backbone, the present invention has a strong agonist activity and has the potential for better treatment of metabolic diseases than many GLP-1/GIP receptor double agonists in this field. Agonistic activity of polypeptide compounds coupled to fatty acid for human GLP-1R and human GIPR receptors.

TABLE 5

| Compound | Fatty acid modification site | Fatty acid chain length | Activity for human GLP-1R ($EC_{50}$ nM) | Activity for human GIPR ($EC_{50}$ nM) |
|---|---|---|---|---|
| Natural GLP-1 | / | / | 0.007 | N/A |
| Natural GIP | / | / | N/A | 0.003 |
| Semaglutide | 20 | 18 | 0.025 | >10 |
| 25 | 40 | 18 | 0.031 | 0.059 |
| 27 | 20 | 18 | 0.12 | 0.11 |
| 28 | 40 | 18 | 0.074 | 0.020 |
| 29 | 30 | 18 | 0.240 | 0.015 |
| 30 | 20 | 18 | 0.058 | 0.021 |
| 60 | 20 | 18 | 0.20 | 0.020 |
| 62 | 40 | 18 | 0.32 | 0.045 |
| 74 | 40 | 20 | 0.068 | 0.046 |
| 75 | 20 | 20 | 0.20 | 0.16 |
| 83 | 40 | 20 | 0.028 | 0.032 |

Experimental Conclusion

The invention found that the activity changes of different peptide skeletons after conjugated to fatty acids are not the same, and the peptide skeleton of the present invention can still maintain favorable activity on GLP-1 and GIP receptors after coupling to fatty acid modification.

3.3 Stability of the Polypeptide Backbone and Polypeptide Compound Coupled to Fatty Acid The stability in plasma is very important for therapeutic polypeptide agents, because polypeptide agents are likely to be sensitive to polypeptide hydrolase and proteolytic enzymes in plasma. The instability of the polypeptides in plasma will affect the half-life and efficacy thereof.

3.3.1 The Purpose of the Experiment

The purpose of this experiment is to test the stability of the numbered compounds in plasma. In order to compare the stability of the numbered compounds with the compounds in the prior art, the preferred polypeptide backbone compounds 023 (H23) and 024 (H24) and the preferred modified compound 089 (H89) taught in the patent application WO2012/167744 were also tested in this experiment.

3.3.2 Experimental Method

Five microliters of samples with concentrations of 20, 50, 100, 200, 500, 1000, 2000, 5000, 10000 ng/ml were added into 45 microliters of SD rat plasma, and the compound contents were detected by LC-MS, and a standard curve was plotted. 5 microliters of the polypeptide solution with a concentration of 1 mg/ml was added into 45 microliters of SD rat plasma. Five samples were prepared for each test compound, and 1 sample was taken out at 0 min, 30 min, 60 min, 120 min, and 240 min respectively. The content of the residual compounds was detected by LC-MS. The content at 0 min was used as control (100%), and the relative contents of the residual compound in the sample at other time points were calculated. The LC-MS method for the detection of the compounds was as follows: 5% acetonitrile solution was prepared as solution A, and 95% acetonitrile solution was prepared as solution B; 15 microliters of samples were injected at a flow rate of 0.6 ml/min, the time duration and the solution gradient ratio were as shown in the following table; the content of the compound was detected with Raptor Biphenyl 2.7 micron detection column.

| Time duration (minutes) | A (%) | B (%) |
| --- | --- | --- |
| 0.20 | 95.0 | 5.00 |
| 1.70 | 5.00 | 95.0 |
| 2.00 | 5.00 | 95.0 |
| 2.01 | 95.0 | 5.00 |
| 2.50 | 95.0 | 5.00 |

3.3.3 Experimental Results

1) Through the above experimental methods, the stability data of the polypeptide backbone in plasma are shown in Table 6:

TABLE 6

| Compound | Relative content of the residual compounds in plasma (%) | | | | |
| --- | --- | --- | --- | --- | --- |
| number | 0 min | 30 min | 60 min | 120 min | 240 min |
| 14 | 100.00 | 106.04 | 107.00 | 112.14 | 102.16 |
| 63 | 100.00 | 99.31 | 98.56 | 109.18 | 108.30 |
| H23 | 100.00 | 86.75 | 88.43 | 93.56 | 84.61 |
| H24 | 100.00 | 99.22 | 93.19 | 89.30 | 85.56 |

3.3.4 Experimental Conclusion

Through research, it is found that the compounds of the present invention can maintain the stability of plasma content (relative content>95%), indicating that the compounds of the present invention have desirable druggability and have favorable potential for the treatment of diseases. The plasma stability of the compounds of the present invention is superior to that of the compounds H23 and H24 in the prior art.

2) Through the above experimental methods, the plasma stability data of the polypeptides coupled to fatty acid are shown in Table 7:

TABLE 7

| Compound | Relative content of the residual compounds in plasma (%) | | | | |
| --- | --- | --- | --- | --- | --- |
| number | 0 min | 30 min | 60 min | 120 min | 240 min |
| 74 | 100.00 | 95.54 | 104.74 | 100.10 | 91.16 |
| 75 | 100.00 | 101.51 | 92.07 | 84.74 | 57.83 |
| H89 | 100.00 | 87.94 | 88.44 | 90.56 | 81.97 |

Experimental Conclusion

It is found that compound 74 of the present invention is more stable in plasma at a time point of 4 hour (relative content>90%) than compound 75 and the prior art compound H89.

3.4 Pharmacokinetics of the Polypeptides Coupled to Fatty Acids in Mice

Plasma stability is one of the factors that affect the pharmacokinetics of polypeptide agents. The in vivo pharmacokinetics of the polypeptide agents is also affected by factors such as their absorption and clearance in the body.

3.4.1 The Purpose of the Experiment

The purpose of this experiment is to study the in vivo pharmacokinetics in mice (plasma) of the numbered compounds administered by single intravenous injection into Balb/c mice as the test animals.

3.4.2 Experimental Method

Male Balb/c mice weighing 18-30 grams and 7-9 weeks old were purchased from Shanghai Jiesijie Laboratory Animal Co., Ltd. The numbered compounds were prepared with 20 mM citrate buffer (pH=7.0), and then were injected into the mice via tail vein at a dose of 30 nanomoles per kilogram of body weight. 0.2 ml of the blood was sampled at time points of 0 hour, 0.083 hour, 0.25 hour, 0.5 hour, 1 hour, 2 hour, 4 hour, 6 hour, 8 hour, 24 hour and 32 hour. The collected mouse blood was centrifuged at 6000 rpm for 6 minutes at a temperature of 4° C. to isolate plasma. The content of the numbered compound in mouse plasma was detected by the experimental method of Test example 3.3.

3.4.3 Experimental Results

Through the above experimental method, the particular data are shown in Table 8:

TABLE 8

| PK parameters | Unit | Compound 28 | Compound 74 |
|---|---|---|---|
| $T_{1/2}$ | h | 4.7 | 19.5 |
| AUCInf | h*ng/mL | 9500 | 30698 |

3.4.4 Experimental Conclusion

Through research, it is found that the compounds of the present invention have favorable pharmacokinetic characteristics in mice, indicating that they have advantages in the treatment of diseases.

3.5 Pharmacokinetics of the Polypeptides Coupled to Fatty Acids in Rats

3.5.1 The Purpose of the Experiment

In order to further study the pharmacokinetics of the compounds of the present invention, this experiment is to study the in vivo pharmacokinetics in rats (plasma) of the numbered compounds administered by single subcutaneous injection into SD rats as the test animals.

3.5.2 Experimental Method

Male SD rats weighing 150-300 grams were purchased from Shanghai Jiesijie Laboratory Animal Co., Ltd. The numbered compounds were prepared with 20 mM citrate buffer (pH=7.0), and then were injected into the rat via subcutaneous injection at a dose of 50 nanomoles per kilogram of body weight. 0.2 ml of the blood was sampled at time points of 0 hour, 0.5 hour, 1 hour, 2 hour, 4 hour, 6 hour, 8 hour, 24 hour, 32 hour, 48 hour, 72 hour, 96 hour and 120 hour. The collected rat blood was centrifuged at 6000 rpm for 6 minutes at a temperature of 4° C. to isolate plasma. The content of the numbered compound in rat plasma was detected by the experimental method of Test example 3.3.

3.5.3 Experimental Results

Through the above experimental method, the particular data are shown in Table 9:

TABLE 9

| PK parameters | Unit | Compound 74 |
|---|---|---|
| $T_{1/2}$ | h | 15.9 |
| AUCInf | h*ng/mL | 17673 |

3.5.4 Experimental Conclusion

Through research, it is found that the compounds of the present invention have favorable pharmacokinetic characteristics in murine, indicating that they have advantages in the treatment of diseases.

3.6 In Vivo Efficacy of Polypeptides Coupled to Fatty Acid

3.6.1 The Purpose of the Experiment

In order to test the effect of subcutaneous administration of the numbered compounds on regulating the blood glucose in diet-induced obesity mice.

3.6.2 Experimental Method

High fat food-induced obesity C57BL/6 mice (male, weighing 35-55 grams and 10-12 weeks old) were purchased from Shanghai Jiesijie Laboratory Animal Co., Ltd. The diet-induced obesity C57BL/6 mice were subcutaneously injected with the numbered compounds (3 nanomol/kg body weight), and then the mice were fasted but freely access to water. After 18 hours, glucose solution with the concentration of 0.2 g/ml was injected intraperitoneally at a dose of 2 g/kg body weight. According to the experimental design, blood was sampled from the tail of the mouse at time points of 0 min, 15 min, 30 min, 60 min, and 120 min to measure the blood glucose levels. Specifically, mouse was physically fixed and the tail was exposed, the tip of tail was cut off, and squeezed until bleeding. The first drop of blood was discarded, and then the blood glucose level was measured with ACCU-CHEK Active (Roche). The area under curve (AUC) of the blood glucose was calculated based on the result of each point.

3.6.3 Experimental Results

Through the above experimental method, the particular data are shown in Table 10:

TABLE 10

| Test compound | Dose | Blood glucose (mmol/L, Mean ± SD) | | | | | AUC (mmol/L · hr) |
|---|---|---|---|---|---|---|---|
| | | 0 min | 15 min | 30 min | 60 min | 120 min | |
| Placebo | | 9.2 ± 0.8 | 25.0 ± 3.1 | 31.6 ± 2.0 | 30.7 ± 1.9 | 25.3 ± 5.4 | 54.9 ± 5.2 |
| 74 | 3 nmol/kg | 3.8 ± 0.8 | 9.6 ± 1.0 | 6.6 ± 1.1 | 4.8 ± 0.6 | 3.3 ± 0.5 | 10.6 ± 1.1 |
| H89 | 3 nmol/kg | 6.9 ± 1.2 | 20.3 ± 3.9 | 24.0 ± 4.4 | 21.2 ± 4.4 | 14.0 ± 3.3 | 37.8 ± 6.6*** |
| Semaglutide | 3 nmol/kg | 4.5 ± 0.5 | 12.7 ± 1.5 | 9.9 ± 0.4 | 7.4 ± 1.4 | 5.3 ± 0.4 | 15.6 ± 1.7** |

***significant difference compared to the blood glucose AUC of compound 74, P = 0.0001.

**significant difference compared to the blood glucose AUC of compound 74, P = 0.002.

35

3.6.4 Experimental Conclusion

In this experiment, the compounds of the present invention show a significant hypoglycemic effect at a dose of 3 nanomol/kg body weight, and the AUC of the blood glucose for compound 74 group was decreased by more than 80% compared to that of placebo. The blood glucose AUC is significantly different, when compared to those of compound H89 and semaglutide that have GLP-1 activity in the prior art.

What claimed is:

1. A GLP-1 analog of formula (I) or a pharmaceutically acceptable salt form thereof:

(R1-SEQ ID NO: 84-R2)   (I)

$R_1$-$X_1$-$X_2$-Glu-Gly-Thr-Phe-Thr-Ser-Asp-$X_{10}$-Ser-$X_{12}$-

Tyr-Leu-$X_{15}$-$X_{16}$-$X_{17}$-$X_{18}$-$X_{19}$-$X_{20}$-Glu-Phe-$X_{23}$-$X_{24}$-

Trp-Leu-$X_{27}$-$X_{28}$-$X_{29}$-$X_{30}$-Pro-Ser-Ser-Gly-Ala-Pro-

Pro-Pro-Ser-$X_{40}$-$R_2$ wherein:

$R_1$ is H, alkyl, acetyl, formyl, benzoyl, trifluoroacetyl, pGlu or absent;

$R_2$ is —$NH_2$, —OH, or absent;

$X_1$ is Tyr;

$X_2$ is Aib;

$X_{10}$ is Tyr;

$X_{12}$ is Ile;

$X_{15}$ is Glu;

$X_{16}$ is Lys;

$X_{17}$ is Ile;

$X_{18}$ is Ala;

$X_{19}$ is Ala, Aib or Gln;

$X_{20}$ is Gln, Glu, Lys or Y1;

$X_{23}$ is Ile or Val;

$X_{24}$ is Ala, Asn or Gln;

$X_{27}$ is Leu;

$X_{28}$ is Ala;

$X_{29}$ is Gly;

$X_{30}$ is Gly, Lys or Y1;

$X_{40}$ is Lys or Y1;

Y1 is Lys, Orn, Dap, Dab or Cys residue, in which a side chain of Y1 is coupled to a substituent shown as formula of {[2-(2-amino-ethoxy)-ethoxy]-acetyl}$_a$-(y-Glu)$_b$-CO—$(CH_2)_c$—COOH;

a is 2;

b is 1 or 2; and c is an integer between 16-20.

2. The GLP-1 analog or the pharmaceutically acceptable salt thereof according to claim 1, characterized in that:

$X_{19}$ is Ala, Aib or Gln;

$X_{20}$ is Gln, Lys or Y1;

$X_{23}$ is Ile or Val;

$X_{24}$ is Ala, Asn or Gln;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of {[2-(2-amino-ethoxy)-ethoxy]-acetyl}$_a$-(y-Glu)$_b$-CO—$(CH_2)_c$—COOH;

a is 2;

b is 1 or 2; and c is an integer between 16-20.

3. The GLP-1 analog or the pharmaceutically acceptable salt thereof according to claim 1, characterized in that:

$X_{19}$ is Ala or Gln;

$X_{20}$ is Gln, Glu, Lys or Y1;

$X_{23}$ is Val;

$X_{24}$ is Ala, Asn or Gln;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

4. The GLP-1 analog or the pharmaceutically acceptable salt thereof according to claim 1, characterized in that:

$X_{19}$ is Ala or Gln;

$X_{20}$ is Gln, Lys, or Y1;

$X_{23}$ is Val;

$X_{24}$ is Asn or Gln;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

5. The GLP-1 analog or the pharmaceutically acceptable salt thereof according to claim 1, characterized in that:

$X_{19}$ is Ala;

$X_{20}$ is Gln, Lys, or Y1;

$X_{23}$ is Val;

$X_{24}$ is Asn;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

6. The GLP-1 analog or the pharmaceutically acceptable salt thereof according to claim 1, characterized in that:

$X_{19}$ is Ala;

$X_{20}$ is Gln, Lys, or Y1;

$X_{23}$ is Val;

$X_{24}$ is Asn;

$X_{30}$ is Gly, Lys or Y1;

$X_{40}$ is Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

7. The GLP-1 analog or the pharmaceutically acceptable salt thereof according to claim 1, characterized in that:

$X_{19}$ is Ala;

$X_{20}$ is Gln;

$X_{23}$ is Val;

$X_{24}$ is Asn;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

8. The GLP-1 analog or the pharmaceutically acceptable salt thereof according to claim 1, characterized in that:

$X_{19}$ is Ala;

$X_{20}$ is Lys;

$X_{23}$ is Val;

$X_{24}$ is Asn;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

9. The GLP-1 analog or the pharmaceutically acceptable salt thereof according to claim 1, characterized in that:

$X_{19}$ is Ala;

$X_{20}$ is Y1;

$X_{23}$ is Val;

$X_{24}$ is Asn;

$X_{30}$ is Gly, Lys or Y1;

$X_{40}$ is Lys or Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2; and b is 1 or 2; and c is an integer between 16-20.

10. The GLP-1 analog or the pharmaceutically acceptable salt thereof according to claim 1, characterized in that:

$X_{19}$ is Ala;

$X_{20}$ is Gln;

$X_{23}$ is Val;

$X_{24}$ is Asn;

$X_{30}$ is Gly or Y1;

$X_{40}$ is Lys or Y1;

Y1 is Lys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

11. The GLP-1 analog or the pharmaceutically acceptable salt thereof according to claim 1, wherein $X_{20}$, $X_{30}$ and $X_{40}$ are each independently Y1;

Y1 is Lys, Orn, Dap, Dab or Cys, in which a side chain of Y1 is coupled to a substituent shown as formula of $\{[2\text{-}(2\text{-amino-ethoxy})\text{-ethoxy}]\text{-acetyl}\}_a\text{-}(y\text{-Glu})_b\text{-}CO\text{—}(CH_2)_c\text{—COOH}$;

a is 2;

b is 1 or 2; and c is an integer between 16-20.

12. The GLP-1 analog or the pharmaceutically acceptable salt thereof according to claim 1, characterized in that, a is 2, b is 1 or 2, and c is 16, 18 or 20.

13. The GLP-1 analog or the pharmaceutically acceptable salt thereof according to claim 1, characterized in that $X_{40}$ is Y1;

Y1 is Lys, in which a side chain of Y1 is coupled to a substituent shown as formula of $\{[2\text{-}(2\text{-amino-ethoxy})\text{-ethoxy}]\text{-acetyl}\}_a\text{-}(\text{y-Glu})_b\text{-CO}\text{—}(CH_2)_c\text{—COOH};$ a is 2;

b is 1 or 2; and c is 16 or 18.

14. The GLP-1 analog or the pharmaceutically acceptable salt thereof according to claim 1, wherein Y1 is Lys covalently linked to the substituent shown as formula of $\{[2\text{-}(2\text{-amino-ethoxy})\text{-ethoxy}]\text{-acetyl}\}_a\text{-}(\text{y-Glu})_b\text{-CO}\text{—}(CH_2)_c\text{—COOH}$ via the side chain amino group of the Lys by forming an amide bond.

15. The GLP-1 analog or the pharmaceutically acceptable salt thereof according to claim 1, characterized in that Y1 is $K(\text{-OEG-OEG-yGlu-}C_{18}\text{—OH})$, wherein the -OEG-OEG-yGlu-$C_{18}$—OH is

16. The GLP-1 analog or the pharmaceutically acceptable salt thereof according to claim 1, wherein Y1 is Lys covalently linked to the substituent shown as formula of $\{[2\text{-}(2\text{-amino-ethoxy})\text{-ethoxy}]\text{-acetyl}\}_a\text{-}(\text{y-Glu})_b\text{-CO}\text{—}(CH_2)_c\text{—COOH}$ via the ε amino group of the C-terminal of Lys by forming an amide bond.

17. A pharmaceutical composition comprising:

a therapeutic amount of the GLP-1 analog or the pharmaceutically acceptable salt thereof according to claim 1, and a pharmaceutically acceptable excipient or a pharmaceutical carrier.

18. A GLP-1 analog selected from the following compounds:

| SEQ ID NO: | sequence |
|---|---|
| 13 | H-YAibEGTFTSDYSIYLEKIAAKEFVNWLLAGGPSSGAPPPSK-NH$_2$ |
| 14 | H-YAibEGTFTSDYSIYLEKIAAQEFVNWLLAGGPSSGAPPPSK-NH$_2$ |
| 15 | H-YAibEGTFTSDYSIYLEKIAQKEFVNWLLAGGPSSGAPPPSK-NH$_2$ |
| 28 | H-YAibEGTFTSDYSIYLEKIAAQEFVNWLLAGGPSSGAPPPSK(OEG-OEG-yGlu-C18-OH)-NH$_2$ |
| 29 | H-YAibEGTFTSDYSIYLEKIAAQEFVNWLLAGK(OEG-OEG-yGlu-C18-OH)PSSGAPPPS-NH$_2$ |
| 30 | H-YAibEGTFTSDYSIYLEKIAAK(OEG-OEG-yGlu-C18-OH)EFVNWLLAGGPSSGAPPPS-NH$_2$ |
| 34 | H-YAibEGTFTSDYSIYLEKIAQQEFIQWLLAGGPSSGAPPPS-NH$_2$ |
| 36 | H-YAibEGTFTSDYSIYLEKIAAQEFIQWLLAGGPSSGAPPPS-NH$_2$ |
| 39 | H-YAibEGTFTSDYSIYLEKIAibQQEFIQWLLAGGPSSGAPPPS-NH$_2$ |
| 47 | H-YAibEGTFTSDYSIYLEKIAAQEFIQWLLAGGPSSGAPPPSK-NH$_2$ |
| 48 | H-YAibEGTFTSDYSIYLEKIAAQEFINWLLAGGPSSGAPPPS-NH$_2$ |
| 49 | H-YAibEGTFTSDYSIYLEKIAAK(OEG-OEG-yGlu-C18-OH)EFINWLLAGGPSSGAPPPS-NH$_2$ |

-continued

| SEQ ID NO: | sequence |
|---|---|
| 50 | H-YAibEGTFTSDYSIYLEKIAAKEFVNWLLAGK(OEG-OEG-yGlu-C18-OH)PSSGAPPPS-NH$_2$ |
| 51 | H-YAibEGTFTSDYSIYLEKIAAKEFVNWLLAGGPSSGAPPPSK(OEG-OEG-yGlu-C18-OH)-NH$_2$ |
| 52 | H-YAibEGTFTSDYSIYLEKIAAQEFINWLLAGK(OEG-OEG-yGlu-C18-OH)PSSGAPPPS-NH$_2$ |
| 53 | H-YAibEGTFTSDYSIYLEKIAAQEFINWLLAGGPSSGAPPPSK(OEG-OEG-yGlu-C18-OH)-NH$_2$ |
| 54 | H-YAibEGTFTSDYSIYLEKIAQK(OEG-OEG-yGlu-C18-OH)EFVNWLLAGGPSSGAPPPS-NH$_2$ |
| 55 | H-YAibEGTFTSDYSIYLEKIAQKEFVNWLLAGK(OEG-OEG-yGlu-C18-OH)PSSGAPPPS-NH$_2$ |
| 56 | H-YAibEGTFTSDYSIYLEKIAQKEFVNWLLAGGPSSGAPPPSK(OEG-OEG-yGlu-C18-OH)-NH$_2$ |
| 74 | H-YAibEGTFTSDYSIYLEKIAAQEFVNWLLAGGPSSGAPPPSK(OEG-OEG-yGlu-C20-OH)-NH$_2$ |
| 75 | H-YAibEGTFTSDYSIYLEKIAAK(OEG-OEG-yGlu-C20-OH)EFVNWLLAGGPSSGAPPPS-NH$_2$ |
| 78 | H-YAibEGTFTSDYSIYLEKIAAQEFVQWLLAGGPSSGAPPPS-NH$_2$ |
| 81 | H-YAibEGTFTSDYSIYLEKIAAQEFVQWLLAGGPSSGAPPPSK(OEG-OEG-yGlu-C20-OH)-NH$_2$ | or a pharmaceutically acceptable salt thereof.

19. A GLP-1 analog or a pharmaceutically acceptable salt thereof, wherein the GLP-1 analog comprises an amino acid sequence of:

H-YAibEGTFTSDYSIYLEKIAAQEFVNWLLAGG-PSSGAPPPSK (-OEG-OEG-yGlu-C$_{20}$—OH)—NH$_2$ (SEQ ID NO:74);

wherein, the OEG-OEG-yGlu-C$_{20}$—OH is

45

*     *     *     *     *